(12) United States Patent
Varma et al.

(10) Patent No.: US 9,080,063 B2
(45) Date of Patent: Jul. 14, 2015

(54) FIRE RESISTANT GLAZINGS

(75) Inventors: Karikath Sukumar Varma, Southport (GB); Benjamin Michael Stiefvater-Thomas, Chorley (GB)

(73) Assignee: PILKINGTON GROUP LIMITED, St. Helens (GB)

( * ) Notice: Subject to any disclaimer, the term of this patent is extended or adjusted under 35 U.S.C. 154(b) by 382 days.

(21) Appl. No.: 13/261,308

(22) PCT Filed: Dec. 22, 2010

(86) PCT No.: PCT/GB2010/052187
§ 371 (c)(1),
(2), (4) Date: Jun. 5, 2012

(87) PCT Pub. No.: WO2011/077151
PCT Pub. Date: Jun. 30, 2011

(65) Prior Publication Data
US 2012/0263903 A1    Oct. 18, 2012

(30) Foreign Application Priority Data
Dec. 23, 2009   (GB) .................................. 0922503.8

(51) Int. Cl.
*C07C 211/63*    (2006.01)
*E06B 3/67*    (2006.01)
(Continued)

(52) U.S. Cl.
CPC ................ *C09D 1/04* (2013.01); *B32B 17/069* (2013.01); *B32B 17/10935* (2013.01);
(Continued)

(58) Field of Classification Search
None
See application file for complete search history.

(56) References Cited

U.S. PATENT DOCUMENTS 3,475,185 A   10/1969   von Freyhold
3,625,722 A   12/1971   Freyhold
(Continued)

FOREIGN PATENT DOCUMENTS

DE   19 43 115 A1   3/1970
EP   0 620 781       10/1994
(Continued)

OTHER PUBLICATIONS

Beckett et al., "A 11B NMR study of zwitterionic and cationic monoborate complexes with cationic 1,2-diol ligands," Polyhedron 27 (2008) pp. 2226-2230.*
(Continued)

*Primary Examiner* — David Sample
(74) *Attorney, Agent, or Firm* — Marshall & Melhorn, LLC

(57) ABSTRACT

An additive for alkali metal silicate solutions, comprising a quaternary ammonium compound having the general formula (1) $R_1R_2R_3R_4N^+OH^-$, wherein $R_1$, $R_2$, $R_3$ and $R_4$ which may be the same or different represent alkyl groups, hydroxy-substituted alkyl groups, alkaryl groups, hydroxy-substituted alkaryl groups comprising from 1 to 12 carbon atoms, or groups having the general formula $-[CH_2]n-N^+R_5R_6R_7$ wherein n is an integer having a value of from 1 to 12, the group $-[CH_2]n$ may be hydroxy-substituted, and $R_5$, $R_6$ and $R_7$ which may be the same or different represent alkyl groups, hydroxy-substituted alkyl groups, alkaryl groups or hydroxy-substituted alkaryl groups comprising from 1 to 12 carbon atoms; with the proviso that at least one of the groups $R_1$, $R_2$, $R_3$, $R_4$, $R_5$, $R_6$ and $R_7$ represents a hydroxy-substituted alkyl group or a hydroxy-substituted alkaryl group comprising at least 2 carbon atoms wherein the hydroxy substituent is not located on a carbon atom which is bonded to a nitrogen atom.

8 Claims, 11 Drawing Sheets

(51) Int. Cl.
  B32B 17/06   (2006.01)
  C07C 215/40  (2006.01)
  C09K 21/06   (2006.01)
  C09D 1/04    (2006.01)
  B32B 17/10   (2006.01)
  C04B 28/26   (2006.01)
  C09D 5/18    (2006.01)
  C09D 7/12    (2006.01)
  C04B 111/00  (2006.01)
  C08K 5/19    (2006.01)

(52) U.S. Cl.
  CPC .............. C04B 28/26 (2013.01); C07C 211/63 (2013.01); C09D 5/185 (2013.01); C09D 7/1233 (2013.01); C04B 2111/00189 (2013.01); C04B 2111/00482 (2013.01); C08K 5/19 (2013.01)

(56) References Cited

U.S. PATENT DOCUMENTS

| | | | |
|---|---|---|---|
| 3,971,665 A | | 7/1976 | Suzuki et al. |
| 4,006,030 A | * | 2/1977 | Yoshida et al. ............ 427/421.1 |
| 4,173,668 A | | 11/1979 | Hentzelt et al. |
| 4,451,312 A | | 5/1984 | Nolte |
| 4,626,301 A | | 12/1986 | Nolte |
| 4,873,146 A | | 10/1989 | Toussaint et al. |
| 4,982,000 A | * | 1/1991 | Earl et al. ....................... 564/296 |
| 5,565,273 A | | 10/1996 | Egli et al. |
| 5,766,770 A | | 6/1998 | Nolte et al. |
| 5,869,715 A | * | 2/1999 | Nantz et al. ..................... 554/110 |
| 6,063,898 A | | 5/2000 | Endo et al. ...................... 528/411 |
| 6,084,131 A | * | 7/2000 | Hollingsworth et al. ..... 564/296 |
| 6,359,176 B1 | * | 3/2002 | Nakamura et al. ............. 564/292 |
| 6,869,977 B1 | * | 3/2005 | O'Lenick et al. ............. 564/291 |
| 7,189,285 B2 | | 3/2007 | Holland et al. |
| 7,541,496 B2 | * | 6/2009 | Deavenport et al. .......... 564/296 |
| 7,786,022 B2 | | 8/2010 | Hamada et al. |
| 7,947,384 B2 | | 5/2011 | Holland et al. |
| 2003/0127024 A1 | | 7/2003 | Heiberger et al. |
| 2005/0255323 A1 | | 11/2005 | Varma et al. |
| 2007/0051627 A1 | * | 3/2007 | Niinobe et al. ................ 204/518 |
| 2009/0317618 A1 | | 12/2009 | Varma et al. |
| 2010/0283133 A1 | | 11/2010 | Hamada et al. |

FOREIGN PATENT DOCUMENTS

| | | |
|---|---|---|
| GB | 1176400 A | 1/1970 |
| GB | 1213588 A | 11/1970 |
| GB | 1 253 331 A | 11/1971 |
| GB | 1 343 460 A | 1/1974 |
| GB | 1 518 958 A | 7/1978 |
| GB | 2 199 535 A | 7/1988 |
| JP | 2007-112733 A | 5/2007 |
| WO | WO 01/70495 A1 | 9/2001 |
| WO | WO 2004/014813 A2 | 2/2004 |
| WO | WO 2008/037382 A2 | 4/2008 |

OTHER PUBLICATIONS

B.M. Lok et al; The role of organic molecules in molecular sieve synthesis; Zeolites; 1983; pp. 282-291, vol. 3, Oct. 1, 1983; Elsevier Science Publishing, US; XP002591313.

G. Engelhardt et al; Structure-forming effects of cations in sodium tetramethyl-ammonium silicate solutions. A silicon-29 NMR study; Journal of Molecular Liquids; 1984; pp. 125-131, vol. 27, Jan. 1, 1984; Elsevier, Amsterdam, NL; XP008134418.

James B. Murdoch et al; High-resolution 29 Si NMR study of silicate and aluminosilicate glasses; the efect of network-modifying cations; American Mineralogist; 1985; vol. 70, pp. 332-343; Apr. 1, 1985; Washington, D.C., US; XP008134536.

Stephen D. Kinrade et al; Effect of Alkali-Metal Cations on the Chemistry of Aqueous Silicate Solutions; Inorganic Chemistry 31; 1992; pp. 4558-4563.

* cited by examiner

FIRE RESISTANT GLAZINGS

BACKGROUND OF THE INVENTION

This invention relates to fire resistant glazings, interlayers useful in such glazings, solutions useful in the production of these interlayers, additives useful in the preparation of said solutions, and methods of directing and/or stabilising the diversity and/or distribution of silicate structures in said solutions.

Fire resistant glazings comprising at least one interlayer comprising a silicate waterglass and at least two panes of glass are well known. When these laminates are exposed to a fire, the interlayer intumesces and expands to form a foam. The foam helps to maintain the integrity of the glazing thereby restricting the spread of a fire and also provides a thermally insulating layer which acts as a barrier to infra-red radiation. These glazings can meet the requirements of most applicable building regulations and are widely used in architecture and building.

In order to be useful, the interlayers must be optically clear and retain that clarity throughout the lifetime of the glazing. They must also provide the required degree of fire resistance. Interlayers which comprise a higher proportion of silica impart a higher degree of fire resistance to the glazing but are more difficult to manufacture as optically clear materials.

The interlayers may be manufactured using a variety of processes. The most widely used process involves pouring a silicate waterglass solution onto the surface of a glass pane and drying that solution under carefully controlled conditions. Such processes are described for example in GB 1518958, GB 2199535, U.S. Pat. No. 4,451,312, U.S. Pat. No. 4,626,301 and U.S. Pat. No. 5,766,770. A variant upon this process in which a silicate solution is dried upon a flat surface to form a film which can be separated from that surface and used as an interlayer is described in WO 01/70495. EP 620781 describes a process in which a silicate solution is poured into the space between two opposed glass panes and allowed to self cure to form a fire resistant glazing.

Whatever the method by which they are produced these silicate based interlayers and the waterglass solutions from which they are produced comprise a plurality of silicate anions. The precise composition of the interlayers and thereby their properties, varies with the conditions under which they are produced. The nature of silicate structures in solution may be thought of as silicon surrounded by oxygen in an almost regular tetrahedron. Pure silicic acid, $Si(OH)_4$, however, does not exist in solution. Condensation reactions occur between such units giving rise to siloxane (Si—O—Si) bridges. The silicon-oxygen tetrahedra may therefore share a corner which, in turn, gives rise to a wide variety of silicate structures in solution.

In order to describe such structures it is convenient to adopt the 'Q' nomenclature used by Engelhardt et al. (G. Engelhardt and O. Rademacher, *J. Mol. Liquids,* 1984, 27, 125). The "Q-unit" (for quadrifunctional) represents a $SiO_4$ group with the number of other Q-units directly attached to the one under consideration, indicated by a superscript. Taking the example of the condensation reaction mentioned above, the silicic acid species would be denoted as a $Q^0$ species as the silicon has no siloxane bridges to any other silicon atoms. The dimer formed from the condensation reaction however, would be denoted as $Q^1_2$ as each silicon atom is bonded to one other via a siloxane bridge. Additional condensation reactions give rise to a wide variety of silicate structures, groups of which may be assigned a Q number and hence easily referred to.

A need exists to improve the mechanical properties of silicate interlayers particularly in the elastomeric range of silicate materials. Currently, silicate interlayers are brittle and therefore difficult to handle and cannot be manipulated. Accordingly, a need exists for a silicate solution that has the potential to dry or cure to form a flexible film. It would also be beneficial to control to varying degrees the structural homogeneity of silicate interlayers, thereby controlling cohesion and water distribution throughout the interlayers.

SUMMARY OF THE INVENTION

According to a first aspect of the present invention there is provided an additive for alkali metal silicate solutions, comprising a quaternary ammonium compound having the general formula 1

$$R_1R_2R_3R_4N^+OH^- \qquad 1$$

wherein $R_1$, $R_2$, $R_3$ and $R_4$ which may be the same or different represent alkyl groups, hydroxy-substituted alkyl groups, alkaryl groups, hydroxy-substituted alkaryl groups comprising from 1 to 12 carbon atoms, or groups having the general formula —$[CH_2]n$-$N^+R_5R_6R_7$ wherein n is an integer having a value of from 1 to 12, the group —$[CH_2]n$- may be hydroxy-substituted, and $R_5$, $R_6$ and $R_7$ which may be the same or different represent alkyl groups, hydroxy-substituted alkyl groups, alkaryl groups or hydroxy-substituted alkaryl groups comprising from 1 to 12 carbon atoms;

with the proviso that at least one of the groups $R_1$, $R_2$, $R_3$, $R_4$, $R_5$, $R_6$ and $R_7$ represents a hydroxy-substituted alkyl group or a hydroxy-substituted alkaryl group comprising at least 2 carbon atoms wherein the hydroxy substituent is not located on a carbon atom which is bonded to a nitrogen atom.

The above mentioned additives for silicate solutions serve to impart a degree of control on the structural homogeneity of silicate interlayers prepared using said solutions, and thereby enable the control of the properties of those interlayers and/or of fire resistant glazings comprising those interlayers. It has surprisingly been found that the above additives can be specifically designed to direct and/or stabilise desired diversity and/or distribution of silicate structures in alkali metal silicate solutions and corresponding dried or cured interlayers. This enables the properties of fire resistant interlayers such as cohesion, flexibility, water distribution to be tailored to suit particular needs by controlling the structural homogeneity of said interlayers. This invention also provides improved thermal stability and ageing performance of said interlayers.

It has been determined that the nature and magnitude of these structure directing effects (SDEs) are directly related to the length of the alkyl chains and the frequency of hydroxy substituents in the additives. Namely, the addition to alkali metal silicate solutions of additives with longer alkyl chains results in a greater diversity and/or distribution of silicate structures in the solution. However, this effect can be counteracted by an increased number of hydroxy substituents in the additives which enables said additives to direct and/or stabilise the diversity and/or distribution of silicate structures in alkali metal silicate solutions. These two effects can be utilised in tandem to fine tune the properties of alkali metal silicate solutions and interlayers prepared from said solutions.

The occurrence of aromatic substituents has a somewhat similar silicate SDE to that of alkyl chains in that diversity and distribution is increased. However, the SDEs of aromatic substituents in the additives differ from those of alkyl groups in that aromatic substituents do not favour smaller silicate structures ($Q^0$ to $Q^2_3$). Aromatic substituents do not direct towards monodisperse solutions, but do direct towards larger silicate species (larger than $Q^2_3$), whereas alkyl groups are not as selective in their control of diversity and distribution.

It has been found that an increase in the temperature of alkali metal silicate solutions will generally result in a partial shift in the dynamic equilibrium and consequently an increase in the diversity and/or distribution of the silicate structures contained therein. Accordingly, this effect can be detrimental in cases where less diversity and a narrower distribution are desired. However, the use of the above additives can retard or remove this effect of an increase in temperature, so that the diversity and/or distribution of silicate structures in the solution are not affected. Therefore, the additives are useful for stabilising silicate structures in alkali metal silicate solutions that require heating, for instance when alkali metal silicate solutions are heated upon drying or curing to form an interlayer.

Furthermore, it has been determined that an interlayer obtained from the drying or curing of an alkali metal silicate solution comprises fewer of the smaller $Q''$ silicate structures present in the solution, suggesting that such structures undergo condensation reactions upon drying or curing resulting in larger $Q''$ structures. This effect can be exploited when using the additives of this invention because the SDEs of the additives can be utilised to eliminate smaller $Q''$ structures prior to drying or curing, enabling the formation of larger $Q''$ silicate structures, in a greater proportion and/or more controlled manner than could normally be obtained in the resultant interlayers.

At least one, at least two or at least three of the groups $R_1$, $R_2$, $R_3$ and $R_4$ may represent groups having the general formula —$[CH_2]n$-$N^+R_5$, $R_6$, $R_7$ wherein n is an integer having a value of from 1 to 12, the group —$[CH_2]n$- may be hydroxy-substituted, and $R_5$, $R_6$ and $R_7$ which may be the same or different represent alkyl groups, hydroxy-substituted alkyl groups, alkaryl groups or hydroxy-substituted alkaryl groups comprising from 1 to 12 carbon atoms.

In some embodiments at least two, preferably at least three, more preferably at least four of the groups $R_1$, $R_2$, $R_3$, $R_4$, $R_5$, $R_6$ and $R_7$ represent a hydroxy-substituted alkyl group or a hydroxy-substituted alkaryl group comprising at least 2 carbon atoms wherein the hydroxy substituent is not located on a carbon atom which is bonded to a nitrogen atom.

$R_1$, $R_2$, $R_3$ and $R_4$ which may be the same or different may represent alkyl groups, hydroxy-substituted alkyl groups, alkaryl groups, or hydroxy-substituted alkaryl groups comprising from 1 to 8 carbon atoms, preferably from 1 to 6 carbon atoms, more preferably from 1 to 4 carbon atoms. In some embodiments, $R_1$, $R_2$, $R_3$ and $R_4$ which may be the same or different may represent alkyl groups, hydroxy-substituted alkyl groups, alkaryl groups, or hydroxy-substituted alkaryl groups comprising from 3 to 8 carbon atoms, preferably from 3 to 6 carbon atoms, more preferably 3 or 4 carbon atoms.

At least one of the groups $R_1$, $R_2$, $R_3$ or $R_4$ may represent a group having the general formula —$[CH_2]n$-$N^+R_5$, $R_6$, $R_7$ wherein n is an integer having a value of from 1 to 8, preferably a value of from 1 to 6, more preferably a value of from 1 to 4.

A preferred group of compounds having the general formula 1 are those which comprise at least two hydroxy substituents, preferably at least three hydroxy substituents, more preferably at least four hydroxy substituents, even more preferably at least five hydroxy substituents.

At least two of the groups $R_{1-7}$ may be hydroxy substituted, preferably at least three of the groups $R_{1-7}$ are hydroxy substituted, more preferably at least four of the groups $R_{1-7}$ are hydroxy substituted, even more preferably at least five of the groups $R_{1-7}$ are hydroxy substituted.

At least one of the groups $R_{1-7}$ may comprise at least two hydroxy substituents, at least three hydroxy substituents, more preferably at least four hydroxy substituents.

The hydroxy substituents may each be located upon different carbon atoms. Without wishing to be bound by any theory the applicants believe that the separation of the hydroxyl substituents contributes to the stability and order which they confer upon the silicate solution.

When at least one of the groups $R_1$, $R_2$, $R_3$ or $R_4$ represents a group having the general formula —$[CH_2]n$-$N^+R_5R_6R_7$, and each nitrogen is substituted with two methyl groups, the group —$[CH_2]n$- may be hydroxy substituted. When the groups $R_{1-3}$ are —$C_2H_4OH$ groups, $R_4$ may be —$CH_2OH$, or a hydroxy-substituted or hydroxy-unsubstituted alkyl or alkaryl group comprising from 2 to 12 carbon atoms.

When the groups $R_1$ and $R_2$ are both —$C_2H_4OH$ groups, $R_3$ and $R_4$ which may be the same or different may be a hydroxy-substituted or hydroxy-unsubstituted alkyl or alkaryl group comprising from 1 to 12 carbon atoms, provided that when $R_3$ and $R_4$ comprise 2 carbon atoms each, at least one of $R_3$ and $R_4$ is hydroxy-substituted.

These additives may conveniently be synthesised by the reaction of a tertiary amine having the general formula $R_1R_2R_3N$ with an alkyl halide having the general formula $R_4Z$, wherein Z represents a halogen atom, to form a tetraalkyl ammonium halide. This halide can be converted to the corresponding hydroxide using an anion exchange resin.

The product of these syntheses is an aqueous solution of the quaternary ammonium compound. The concentration of this solution will generally be in the range 20% wt to 50% wt of solid material. Such a solution may be readily mixed with an aqueous solution of an alkali metal silicate waterglass.

According to another aspect the present invention provides a stable aqueous solution for the production of fire resistant glazings comprising:
at least one alkali metal silicate,
at least one additive in accordance with the first aspect of the present invention, and water.

The production of fire resistant laminated glazings having a waterglass based interlayer has been described in a number of patents including British Patents GB 1518598 and GB 2199535, U.S. Pat. No. 4,451,312, U.S. Pat. No. 4,626,301 and U.S. Pat. No. 5,766,770. U.S. Pat. No. 4,626,301 and U.S. Pat. No. 5,766,770 further disclose the incorporation of a polyhydric organic compound into the waterglass solution. The organic compound serves to reduce the incidence of cracking at the surface of the dried interlayer and in a fire serves to improve the fire resistance of the laminate by forming a char which tends to preserve the integrity of the laminate.

The at least one alkali metal silicate may be a sodium and/or a potassium silicate. Any of the sodium silicate waterglasses which are known to be useful in the art may be used in this invention. The sodium silicates may be those wherein the weight ratio of $SiO_2:Na_2O$ is at least 1.6:1 and preferably is in the range 2.0:1 to 6.0:1, more usually in the range 2.0:1 to 4.0:1. These preferred silicates are those wherein the weight ratio $SiO_2:M_2O$ is in the range 2.5 to 4.0. Sodium silicate waterglass solutions having a weight ratio of $SiO_2:Na_2O$ in the range 2:1 to 4:1 are available as articles of commerce. Specifically solutions wherein this ratio is 2.0:1, 2.5:1, 2.85:1, 3.0:1 and 3.3:1 are available as articles of commerce. Solutions having a weight ratio of $SiO_2:Na_2O$ between these values may be produced by blending these commercially available materials.

Potassium silicate and lithium silicate waterglass solutions may also be used to produce the interlayers of this invention. In general they will be used as a partial replacement for the sodium silicate waterglass and the molar ratio of sodium ions to the total of potassium and/or lithium ions may be at least 2:1. Where a potassium silicate waterglass is used it is preferably one in which the molar ratio of $SiO_2:K_2O$ is in the range 1.4:1 to 2.5:1.

In a preferred embodiment the alkali metal silicate waterglass solution used to produce an interlayer according to this invention of this invention comprises a mixture of a sodium silicate waterglass and a potassium silicate waterglass. More preferably such solutions comprise a mixture in which the molar ratio of sodium ions to potassium ions is at least 3:1 and most preferably at least 4:1.

The solutions of this invention will preferably comprise a relatively high proportion of solid materials. The solutions are stable aqueous solutions which can be dried or cured to form transparent interlayers. The preferred solutions useful according to this invention comprise from 30 to 60% by weight of solid materials. Waterglass solutions comprising from 35 to 40% by weight of solid materials are commercially available and are thereby preferred for use in the present invention.

The additive may be present in an amount of from 0.01% to 10% by weight of the solution. Preferably the additive will be present in an amount of from 0.1% to 5% by weight of the solution and most preferably in the region 0.25% to 2% by weight of the solution.

The solutions of this invention may further comprise one or more of the polyhydric organic compounds which are known in the art to be useful adjuvants. Polyhydric compounds which have been proposed for use include glycerol, a derivative of glycerol or a mono or a polysaccharide, in particular a sugar. The most commonly used polyhydric compound and the preferred compound for use in the present invention is glycerol.

The solutions of this invention may comprise from 4 to 12% by weight of a polyhydric organic compound. The solutions of this invention may comprise from 30 to 85% by weight of water.

According to another aspect of the present invention there is provided a transparent intumescent interlayer for the production of fire resistant glazings comprising:
at least one alkali metal silicate,
at least one additive in accordance with the first aspect of the present invention, and water.

The above mentioned additives for silicate solutions serve to impart a degree of control on the structural homogeneity of silicate interlayers prepared using said solutions, and thereby enable the control of the properties of those interlayers and/or of fire resistant glazings comprising those interlayers.

As detailed above, the properties of the additives of this invention can be exploited to enable control of the structural homogeneity, cohesion and water distribution of the interlayers of the present invention, yielding enhanced fire resistance and ageing properties of those interlayers and/or of fire resistant glazings comprising those interlayers.

The interlayer may comprise from 10 to 50% by weight of water. Furthermore, the interlayer may comprise from 12 to 20% by weight of a polyhydric organic compound.

The thickness of the interlayer will generally be in the range 0.5 to 2.0 mm for interlayers prepared using a pour and dry process. An interlayer thickness of 4 to 5 mm is usually employed for interlayers produced via a cast in place process. The formulation of thicker interlayers requires longer drying times and is thereby disadvantageous. Thinner interlayers require correspondingly shorter drying times. Laminates having a thicker interlayer may be produced by bringing two sheets of glass, each having a thinner interlayer, for instance from 0.5 to 1.0 mm thick, into face to face contact so as to form an interlayer which may be for example from 1.0 to 2.0 mm thick.

According to another aspect of the present invention there is provided a fire resistant glazing comprising at least one interlayer according to the invention attached to at least one glass sheet.

Fire resistant glazings comprising an intumescent interlayer according to this invention will generally comprise an interlayer which is from 1.0 to 3.0 mm thick. The at least one glass sheet will typically be at least one sheet of soda lime float glass. Toughened and laminated float glass may also be used. Other glass compositions may be employed; in particular those having a higher strain temperature as these will increase the fire resistance of the glazing. Glass panes having a functional coating upon one or both surfaces may also be used. The coated surface may be on the inside or the outside of the glazing. Coatings which are known to absorb UV radiation and/or reflect heat may be especially advantageous. Other coated glass panes which may be used include solar control glasses and self cleaning photoactive glasses.

According to another aspect of the present invention there is provided a fire resistant glazing assembly comprising at least one fire resistant glazing according to the invention attached to a frame.

According to another aspect of the present invention there is provided a building incorporating at least one fire resistant glazing according to the invention.

According to another aspect of the present invention there is provided a method of preparing an additive according to the invention comprising:
adding an alkyl halide or an alkarylhalide to an alkanolamine or an alkarylamine, purification of the resultant halide compound, and
conversion of said halide compound to the corresponding additive.

The conversion of the halide compound to the corresponding additive may be achieved using an ion exchange resin.

According to another aspect of the present invention there is provided a method of preparing a transparent interlayer according to the invention comprising:
drying or curing under controlled conditions a stable aqueous solution in accordance with the present invention.

According to another aspect of the present invention there is provided a method of preparing a fire resistant glazing according to the invention comprising:
drying or curing under controlled conditions a stable aqueous solution in accordance with the present invention upon at least one glass sheet.

The interlayer of the present invention may be produced by drying or curing a solution of the present invention. The solutions may be dried to form transparent intumescent interlayers and/or fire resistant glazings using conventional techniques.

When the evaporation is complete the coated glass sheet may be removed from the oven. The resulting product is a fire resistant glazing comprising an interlayer attached to a glass sheet.

The water content of the solution may then be reduced during the drying step to a level which is in the range 10 to 50% by weight of the total weight of the dried interlayer. The concentrations of the silicate, the additive and, optionally, the polyhydric compound are correspondingly increased.

A second sheet of glass may be bonded to the dried interlayer to produce a laminated fire resistant glazing. Alternatively a second sheet of glass having a dried interlayer can be bonded to the interlayer of the first sheet of glass and then a top sheet can be added to form a laminate having two interlayers. This process can be continued to produce however many interlayers are desired. Another alternative is to bond the second sheet with the interlayers in contact with one another and thus form a single interlayer having twice the thickness of the original.

In an alternative process the solutions may be dried on the surface of a substrate and, provided that the interlayer has sufficient mechanical strength, it can be separated from the substrate and placed between two glass sheets to form a fire resistant glazing. Suitable substrates on which the solution could be dried include glass, metals such as stainless steel and polymeric materials such as PTFE and polyolefins such as polypropylene. Where the substrate is transparent e.g. when the substrate is a transparent polymeric film, the film with the interlayer dried upon one surface may be mounted between two glass panes so as to form a fire resistant glazing without the need to separate the dried interlayer from the substrate.

EP 620781 discloses a cast in place method for the production of a fire resistant glazing comprising a silicate interlayer. The method comprises applying a sealant around the entire circumference of two opposed glass panes thereby defining a cavity between them and pouring a silicate solution into that cavity. The silicate solution is then allowed to cure. The curing may be accelerated by raising the temperature of the glazing.

According to a further aspect of the present invention there is provided the use of an additive according to the invention in the preparation of a fire resistant glazing.

According to a further aspect of the present invention there is provided the use of a solution according to the invention in the preparation of a fire resistant glazing.

According to a further aspect of the present invention there is provided the use of a fire resistant glazing according to the invention to prevent the spread of fire.

According to another aspect of the present invention there is provided a method of directing and/or stabilising the diversity and/or distribution of silicate structures in an alkali metal silicate solution comprising:
treating an alkali metal silicate solution with at least one additive capable of directing and/or stabilising the diversity and/or distribution of silicate structures in said solution.

As detailed above, it has surprisingly been found that the diversity and/or distribution of silicate structures in alkali metal silicate solutions can be controlled by using additives that direct and/or stabilise said structures as desired. This is advantageous because it enables fine tuning of the cohesion, flexibility and water distribution properties of alkali metal silicate solutions, and interlayers prepared using said solutions, to the desired fire resistance requirements by controlling the structural homogeneity of said solutions and interlayers.

The method may further comprise analysing the distribution of silicate structures in the alkali metal silicate solution using $^{29}$Si NMR before and/or after the solution is treated with the at least one additive. As the chemical environment of a given silicon nucleus is affected, the electron density around that nucleus is changed. Structural variation in the siloxane skeleton has a marked influence on the electron density around specific silicon atoms. Hence, $^{29}$Si NMR can be used as it permits the direct determination of the structure and relative concentration of a series of distinct silicate anions and silicate structural units present in silicate solutions.

The at least one additive may be a hydroxy-functionalised quaternary ammonium hydroxide comprising alkyl groups, alkaryl groups or a mixture of alkyl and alkaryl groups. At least one alkyl group and/or at least one alkaryl group may be functionalised with at least one hydroxy group, preferably at least two hydroxy groups. The at least one additive may be in accordance with the first aspect of the present invention.

The treatment of the alkali metal silicate solution with at least one additive may affect the stability and/or proportion of $Q^3{}_8$ silicate structures in the solution.

The method may further comprise increasing or reducing the temperature of the solution. As detailed above, it has been found that an increase in the temperature of alkali metal silicate solutions will generally result in a partial shift in the dynamic equilibrium and consequently an increase in the diversity and/or distribution of the silicate structures contained therein. However, the above method can retard or remove this effect of an increase in temperature, so that the diversity and/or distribution of silicate structures in the solution are not affected. Therefore, the above method is useful for stabilising silicate structures in alkali metal silicate solutions that require heating, for instance when alkali metal silicate solutions are heated upon drying or curing to form an interlayer.

As detailed above, it has been determined that an interlayer obtained from the drying or curing of an alkali metal silicate solution comprises fewer of the smaller $Q''$ silicate structures present in the solution, suggesting that such structures undergo condensation reactions upon drying or curing resulting in larger $Q''$ structures. This effect can be exploited when using the method of this invention because the SDEs of the additives can be utilised to eliminate or control the number of smaller $Q''$ structures prior to drying or curing, enabling a more controlled formation of larger silicate structures, in a greater proportion, than could normally be obtained in the resultant interlayers.

It will be appreciated that optional features applicable to one aspect of the invention can be used in any combination, and in any number. Moreover, they can also be used with any of the other aspects of the invention in any combination and in any number. This includes, but is not limited to, the dependent claims from any claim being used as dependent claims for any other claim in the claims of this application.

BRIEF DESCRIPTION OF THE DRAWINGS

Embodiments of the present invention will now be described with reference to the following figures.

DETAILED DESCRIPTION OF THE INVENTION

Figure 1:
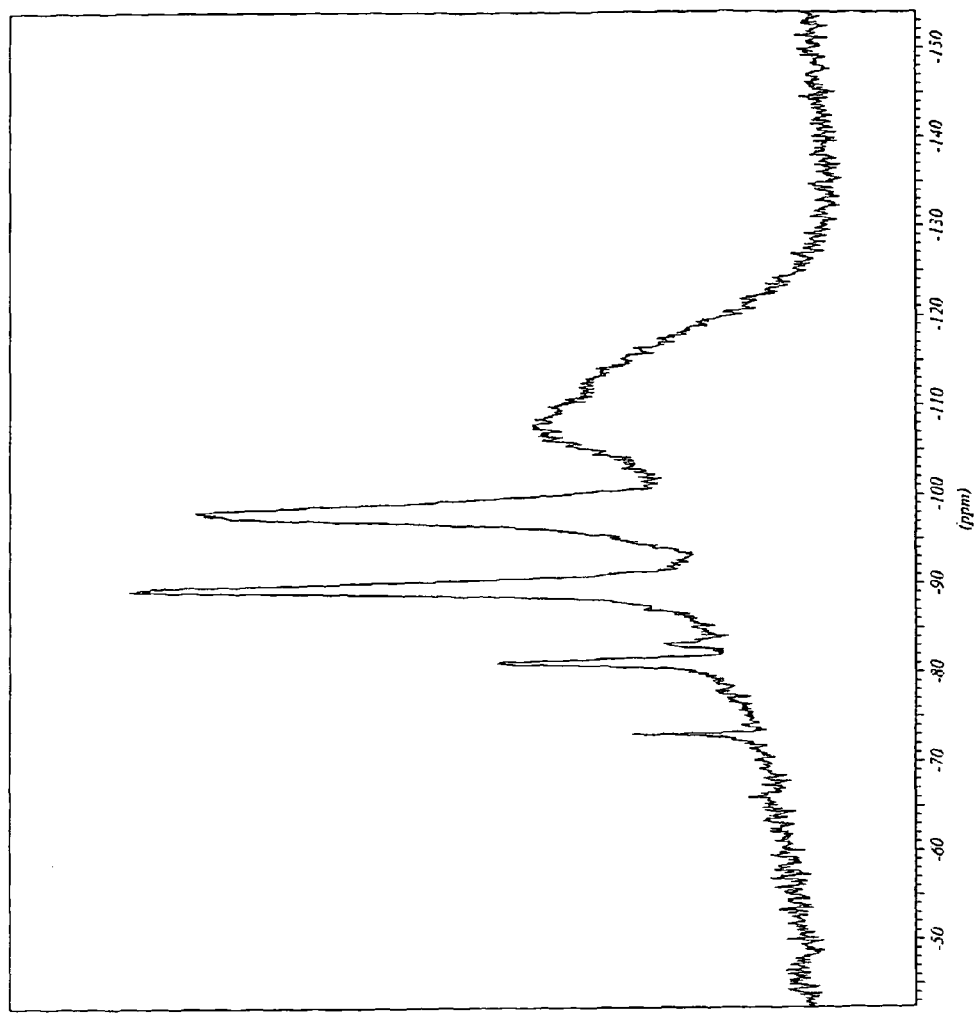
FIG. 1 shows $^{29}$Si NMR spectra of (a) sodium silicate solution 1:1, 2.5M and (b) choline silicate solution 1:1, 2.43M.
Figure 1:
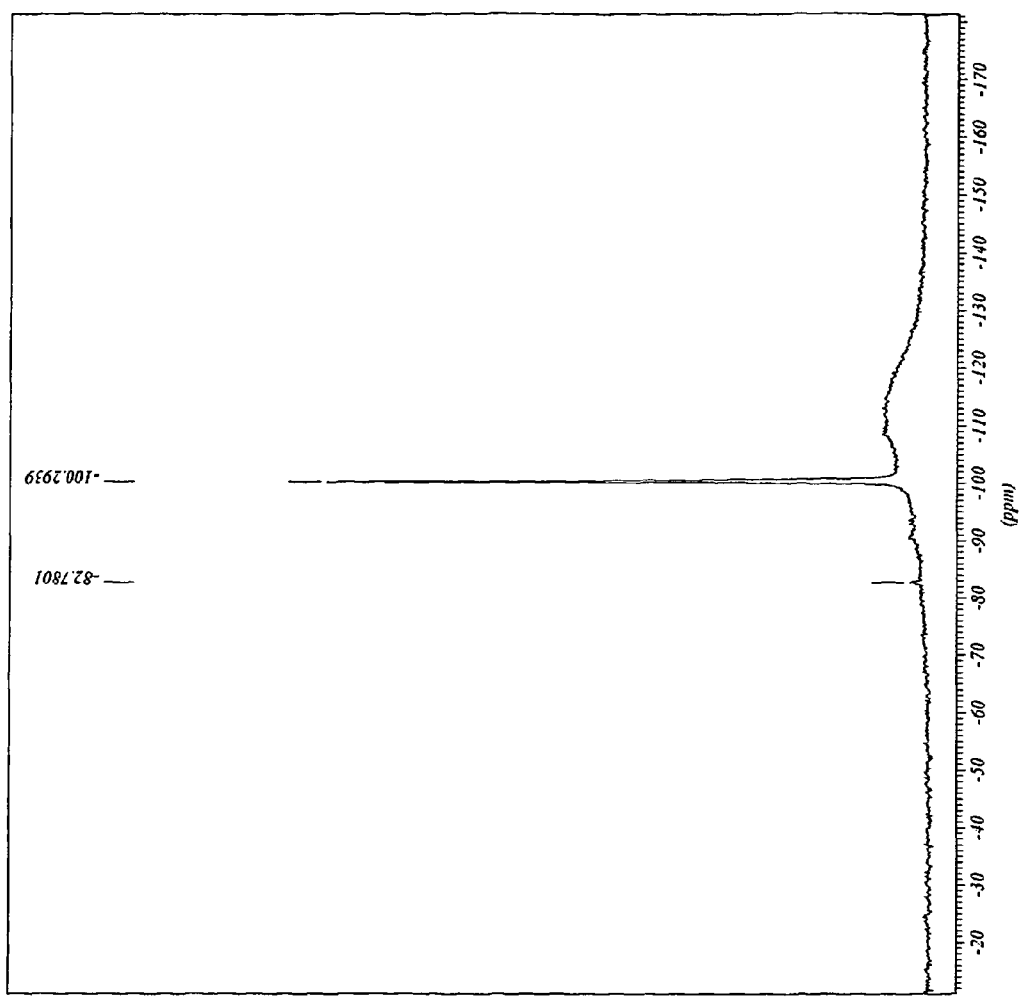

In the studies of the present invention a number of novel hydroxy-substituted quaternary ammonium compounds were synthesised and used to prepare previously unreported quaternary ammonium silicate solutions. These solutions were studied using NMR, and the speciation of mixed alkali metal/quaternary ammonium silicate solutions was investigated.

Preparation of Tetraalkylammonium Halides

Preparation of $[(CH_3)_3N(CH_2CH_2OH)]I$ (2I)

Dimethylethanolamine (40 ml, 35.44 g, 0.39 mol) was cooled in a round bottom flask on an ice bath. To this, methyl iodide (24.3 ml, 55.35 g, 0.39 mol) was slowly added. The reaction was allowed to cool for 5 mins before methanol (40 ml) was added. The solution was then heated to ca. 60° C. overnight. All solvents were then removed on a rotary evaporator to give the white crystalline solid.

Yield=55.85 g (62%)

NMR $\delta(^1H)$/ppm: 7.31 (1H, s), 6.65 (2H, d t), 6.1 (2H, t), 5.77 (9H, s). $\delta(^{13}C)$/ppm: 69.8 ($CH_2OH$), 58.1 ($3\times CH_3$), 56.5 ($CH_2$). Required for $C_5H_{14}INO$: C, 26.0; H, 6.1; N, 6.1. Found: C, 25.6; H, 5.7; N, 6.1.

Analogous processes were used to prepare other TAA halides, the NMR and CHN characterisation data for which are shown below:

$[(CH_3)_2(CH_3CH_2)N(CH_2CH_2OH)]Br$ (3Br)

NMR $\delta(^1H)$/ppm: 7.32 (2H, d), 6.57 (2H, d), 6.0 (2H, d t), 5.7 (1H, s), 5.64 (6H, s), 3.9 (3H, t). $\delta(^{13}C)$/ppm: 66.6 ($CH_2$), 63.3 ($CH_2$), 57.6 ($2\times CH_2$), 53.1 ($CH_2$), 9.9 ($CH_3$). Required for $C_6H_{16}BrNO$: C, 36.4; H, 8.1; N, 7.1. Found: C, 35.9; H, 8.2; N, 7.1.

$[(CH_3)_2(CH_3CH_2CH_2)N(CH_2CH_2OH)]Br$ (4Br)

NMR $\delta(^1H)$/ppm: 7.31 (1H, s), 6.55 (2H, bs), 6.1 (2H, t), 5.9 (2H, t), 5.6 (6H, s), 4.35 (2H, d t), 3.45 (3H, t). $\delta(^{13}C)$/ppm: 69.0 ($CH_2.O$), 67.1 ($CH_2.C$), 57.6 ($2\times CH_2$), 53.6 ($CH_2OH$), 17.9 ($CH_2$), 12.1 ($CH_3$). Required for $C_7H_{18}BrNO$: C, 39.6; H, 8.6; N, 6.6. Found: C, 38.7; H, 8.9; N, 6.5.

$[(CH_3)_2N(CH_2CH_2OH)_2]I$ (5I)

NMR $\delta(^1H)$/ppm: 7.32 (2H, s), 6.9 (4H, dd), 6.25 (4H, t), 5.9 (6H, s). $\delta(^{13}C)$/ppm: 68.8 ($2\times CH_2OH$), 58.1 ($2\times CH_3$), 55.2 ($2\times CH_2$). Required for $C_6H_{16}INO_2$: C, 27.6; H, 6.2; N, 5.4. Found: C, 27.6; H, 6.3; N, 5.4.

$[(CH_3)N(CH_2CH_2OH)_3]I$ (6I)

NMR $\delta(^1H)$/ppm: 7.34 (3H, s), 6.61 (6H, m), 6.28 (6H, t), 5.85 (3H, q). $\delta(^{13}C)$/ppm: 66.9 ($3\times CH_2OH$), 57.7 ($3\times CH_2N$), 52.66 ($CH_3$). Required for $C_7H_{18}INO_3$: C, 28.9; H, 6.2; N, 4.8. Found: C, 28.1; H, 6.5; N, 4.4.

$[(CH_3)_2(CH_2Ph)N(CH_2CH_2OH)]Br$ (8Br)

NMR $\delta(^1H)$/ppm: 10.1 (5H, s), 7.4 (1H, s), 7.1 (2H, s), 6.56 (2H, bs), 6.0 (2H, bs), 5.6 (6H, s). $\delta(^{13}C)$/ppm: 135.4 (ArC), 133.1 ($2\times$ArCH), 131.5 ($2\times$ArCH), 129.4 (ArC), 71.5 ($CH_2$), 67.6 ($CH_2OH$), 57.7 ($2\times CH_3$), 52.6 ($CH_2$). Required for $C_{11}H_{18}BrNO$: C, 50.8; H, 7.0; N, 5.4. Found: C, 50.7; H, 7.1; N, 5.4.

$[(CH_3)(CH_2Ph)N(CH_2CH_2OH)_2]Br$ (9Br)

NMR $\delta(^1H)$/ppm: 10.1 (5H, s), 7.3 (1H, s), 7.1 (2H, s), 6.6 (4H, bs), 6.1 (4H, bs), 5.6 (3H, s). $\delta(^{13}C)$/ppm: 136.2 (ArC), 133.2 ($2\times$ArCH), 131.6 ($2\times$ArCH), 129.2 (ArCH), 70.0 ($CH_2OH$), 65.3 ($CH_2OH$), 57.6 ($2\times CH_2$), 50.8 ($CH_3$). Required for $C_{12}H_{20}BrNO_2$: C, 49.7; H, 6.8; N, 4.9. Found: C, 49.1; H, 6.8; N, 4.9.

$[(CH_3)_2(CH_2CH_2OH)NCH_2CH(OH)CH_2N(CH_3)_2(CH_2CH_2OH)_2]0.2Cl$ (10Cl)

NMR $\delta(^1H)$/ppm: 7.51 (1H, s), 7.32 (2H, s), 6.85 (1H, m), 6.62 (4H, t), 6.24 (4H, d), 6.13 (4H, t), 5.74 (6H, s). $\delta(^{13}C)$/ppm: 69.0 ($2\times CH_2OH$), 67.1 (CHOH), 64.2 ($NCH_2C$), 57.7 ($3\times CH_2N$), 55.1 ($4\times CH_3$). Required for $C_{11}H_{28}Cl_2NO_3$: C, 43.8; H, 7.4; N, 9.3. Found: C, 43.8; H, 7.1; N, 8.9.

$[(CH_3)_2N(CH_2CH_2OH)(CH_2CHOHCH_2OH)]OH$ (7OH)

7OH was prepared using a different process. Glycidol (20.4 ml, 22.78 g, 0.3 mol) was added slowly to dimethylethanolamine (28.2 ml, 24.98 g, 0.28 mol) with cooling supplied by a water bath at 20° C. To this, water (50 ml) was added. Caution: below 20° C. the reaction proceeds very slowly but above 35° C. an uncontrollable exotherm occurs. The solution was left to stir for a minimum of 4 hours but preferably 12-18 hours. After this time the viscosity of the solution had increased. Chloroform (3×20 ml) was used to remove any unreacted amine and/or glycidol. A 1 ml aliquot of the resulting solution (total volume=45.4 ml) was titrated with HCl (0.1M) to establish its cationic content and hence the concentration of the solution (2.025M).

Calculated yield=18.36 g (36%)

NMR $\delta(^{13}C)$/ppm: 70.42, 69.0 ($CH_2N$), 68.1 (CHOH), 66.6 (3-$CH_2OH$), 57.2 (2-$CH_2OH$), 54.4 ($2\times CH_3N$). 69.6, 68.2 ($CH_2N$), 67.7 (CHOH), 65.8 (3-$CH_2OH$), 56.6 (2-$CH_2OH$), 53.8 ($2\times CH_3N$).

Preparation of Tetraalkylammonium Hydroxides

The above TAA halides were converted to the equivalent hydroxide using the anion exchange resin, Dowex 550. The general procedure is described in detail for the exchange of choline iodide to choline hydroxide. The resin (30 g) was activated using NaOH before being thoroughly washed with distilled water. To this was added $[(CH_3)_3N(CH_2CH_2OH)]I$ (1.99 W 8 mmol) in distilled water (50 ml). This was then agitated on a mixing plate for 24 hours. The resin was removed by filtration and further washed with distilled water (4×15 ml). The filtrate and washings were reduced on a rotary evaporator to a volume of 8 ml. The filtrate was shown to contain no halide using the silver nitrate test. An aliquot of the solution (1 ml) was diluted with water (9 ml) and titrated with HCl (0.1M) to establish the hydroxide content as 1.0M. Calculated yield=0.96 g (99%) (1M solution)

Solution Studies of Aqueous Silicates Using $^{29}Si$ NMR

Unlike alkali metal cations, certain quaternary ammonium cations exert specific structure directing effects on the silicate anions present in solution. This is clearly demonstrated by the $^{29}Si$ NMR of sodium and choline, $[(CH_3)_3N(CH_2CH_2OH)]$, silicate solutions as shown in FIG. 1. Although the silica concentrations and cation/silica ratios of both solutions are comparable, a broad distribution of silicate anions is observed in the sodium silicate solution but a single anionic species predominates in the choline silicate solution.

Figure 2:
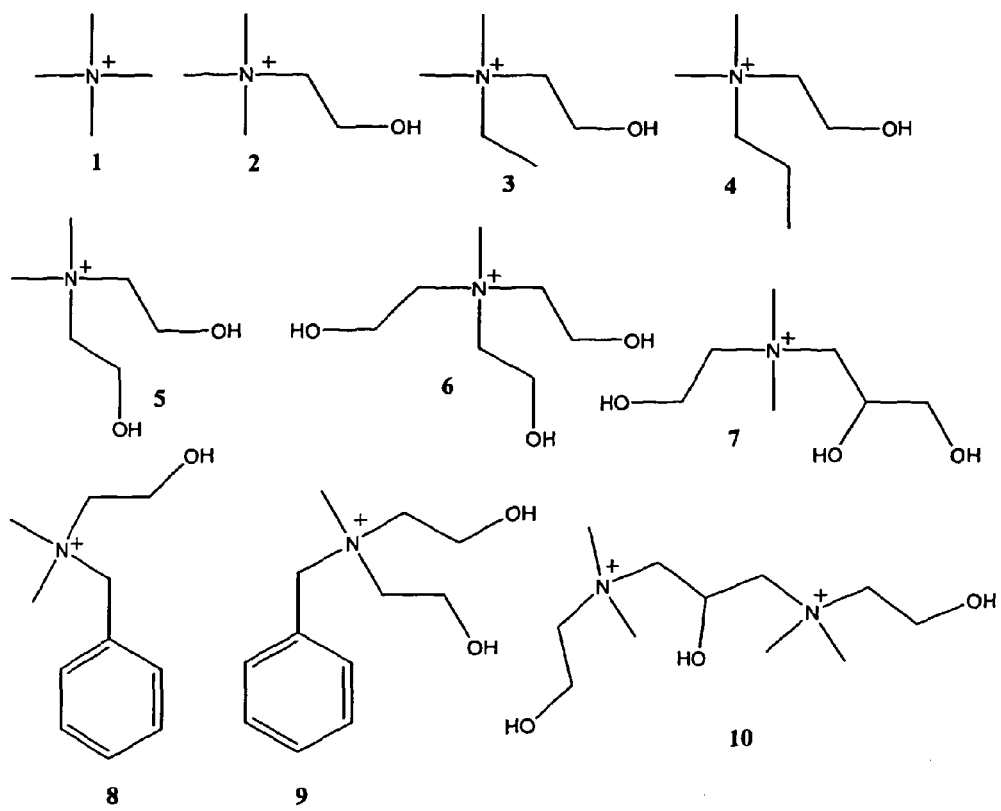
FIG. 2 shows quaternary ammonium cations investigated as examples for the present invention.

The appearance of the sodium silicate spectra is down to the overlapping of many resonance lines each of which corresponds to a specific silicate anion present in solution. In the case of the choline silicate solution an intense peak may be observed at −100 ppm, which may be assigned to the cubic octameric anion, $Q^3{}_8$. The quaternary ammonium cations used in the synthesis of the silicate solutions described herein are shown in FIG. 2. Using the hydroxides of these cations, a number of quaternary ammonium silicates were synthesised and the speciation of silicate structures was investigated by $^{29}Si$ NMR. The results obtained are summarised in Table 1.

TABLE 1

A summary of silicate speciation within a number of TAA silicate solutions.

| Cation | Cation:Si | ≈$_c$[SiO$_2$] | pH | Q$^0$ (%) −73 ppm | Q$^1$ (%) −81/82 ppm | Q$^2_3$ (%) −83 ppm | Q$^2$ (%) −87/91 ppm | Q$^3$ (%) −100 ppm | | Additional |
|---|---|---|---|---|---|---|---|---|---|---|
| 1 | 1:1 | 1.02M | 10 | 0 | 0 | 0 | 0 | 100 |  | Accounts for all the Q$^3$ Signal observed |
|   |   |   |   |   |   |   |   |   | Q$^4$ | Absent |
| 2 | 1:1 | 2.42M | 10 | Trace | Trace | Trace | Trace | 100 |  | Accounts for all the Q$^3$ Signal observed |
|   |   |   |   |   |   |   |   |   | Q$^4$ | Absent |
| 3 | 1:1 | 1.12M | 10 | 9.4 | 5.7 | 3.8 | 20.8 | 60.4 |  | Accounts for all the Q$^3$ Signal observed |
|   |   |   |   |   |   |   |   |   | Q$^4$ | Absent |
| 4 | 1:1 | 0.91M | 10 | 6 | 13 | 6 | 31 | 44 | | Apart from Q$^0$, no specific structures can be identified from the spectra |
| 8 | 1:1 | 0.7M | 10 | Trace | Trace | Trace | 58 | 42 | | No specific structures can be identified from the spectra |
| 5 | 1:1 | 1.6M | 10 | 4.5 | 0 | 0 | 15 | 79.5 | Q$^2$ | Slightly broad signal observed |
|   |   |   |   |   |   |   |   |   |  | Accounts for all the Q$^3$ Signal observed |
|   |   |   |   |   |   |   |   |   | Q$^4$ | Absent |
| 9 | 1:1 | 2.7M | 10 | Trace | Trace | 0 | 31 | 69 |  | Accounts for 8% of the signal observed for Q$^2$ |
|   |   |   |   |   |   |   |   |   |  | Accounts for 23% of the signal observed for Q$^2$ |
|   |   |   |   |   |   |   |   |   |  | Accounts for all the Q$^3$ signal observed |
|   |   |   |   |   |   |   |   |   | Q$^4$ | Absent |
| 6 | 1:1 | 3.97M | 10 | Trace | Trace | 0 | 10 | 90 | Q$^2$ | Broad signal observed |
|   |   |   |   |   |   |   |   |   |  | Accounts for all the Q$^3$ Signal observed |
|   |   |   |   |   |   |   |   |   | Q$^4$ | Absent |
| 7 | 1:1 | 2.42M | 10 | 4 | 0 | 0 | 5 | 91 |  | Accounts for 5% |
|   |   |   |   |   |   |   |   |   |  | Accounts for all the Q$^3$ Signal observed |
|   |   |   |   |   |   |   |   |   | Q$^4$ | Absent |
| 10 | 1:2 | 3.01M | 11 | 3 | Trace | Trace | 14 | 83 | Q$^2$ | Slightly broad signal observed |

TABLE 1-continued

A summary of silicate speciation within a number of TAA silicate solutions.

| Cation | Cation:Si | $\approx_c[SiO_2]$ | pH | $Q^0$ (%) −73 ppm | $Q^1$ (%) −81/82 ppm | $Q^2_3$ (%) −83 ppm | $Q^2$ (%) −87/91 ppm | $Q^3$ (%) −100 ppm | Additional | |
|---|---|---|---|---|---|---|---|---|---|---|
| | | | | | | | | |  | Accounts for all the $Q^3$ Signal observed |
| | | | | | | | | | $Q^4$ | Absent |

Functionalised Quaternary Ammonium Cations with Longer Alkyl or Aromatic Groups, (3), (4), (8) and (9)

Figure 3:
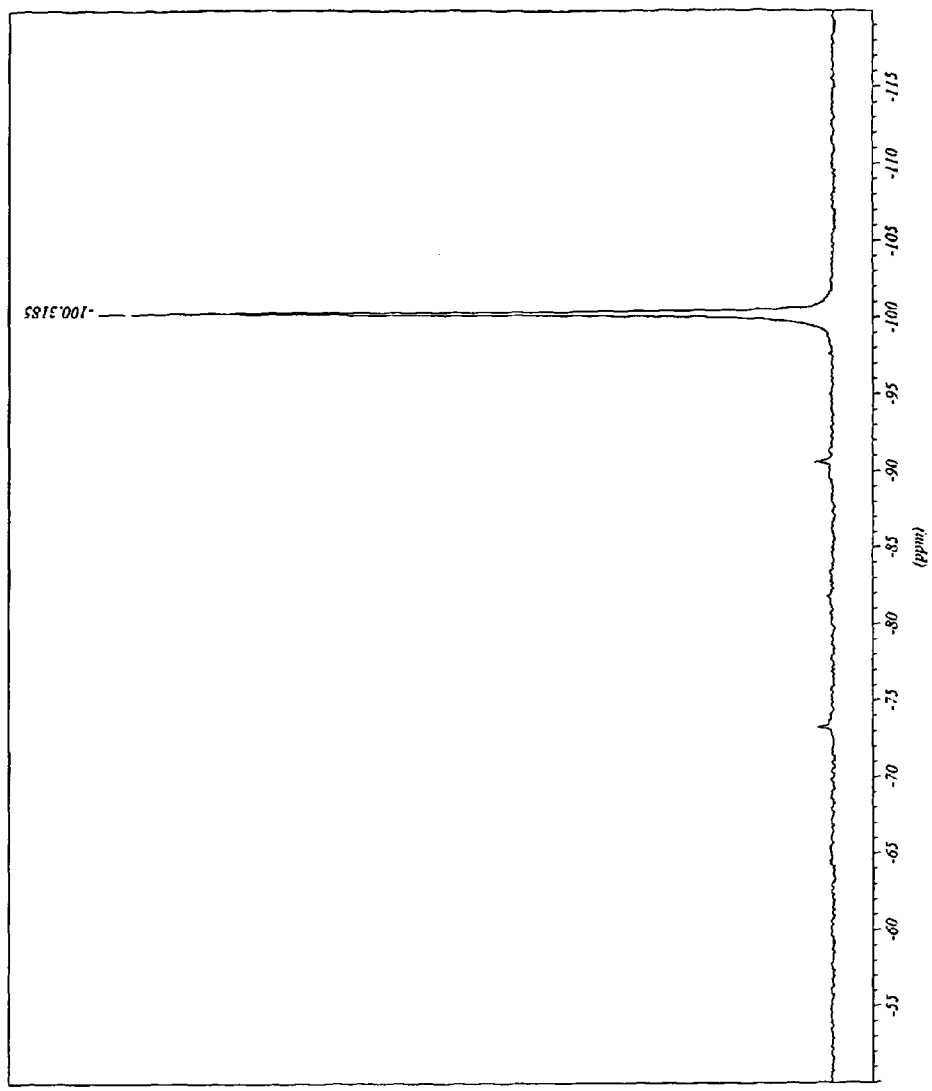
FIG. 3 shows $^{29}$Si NMR spectra of (a) choline (2) silicate 1:1 and (b) ethyl-choline (3) silicate 1:1.
Figure 3:
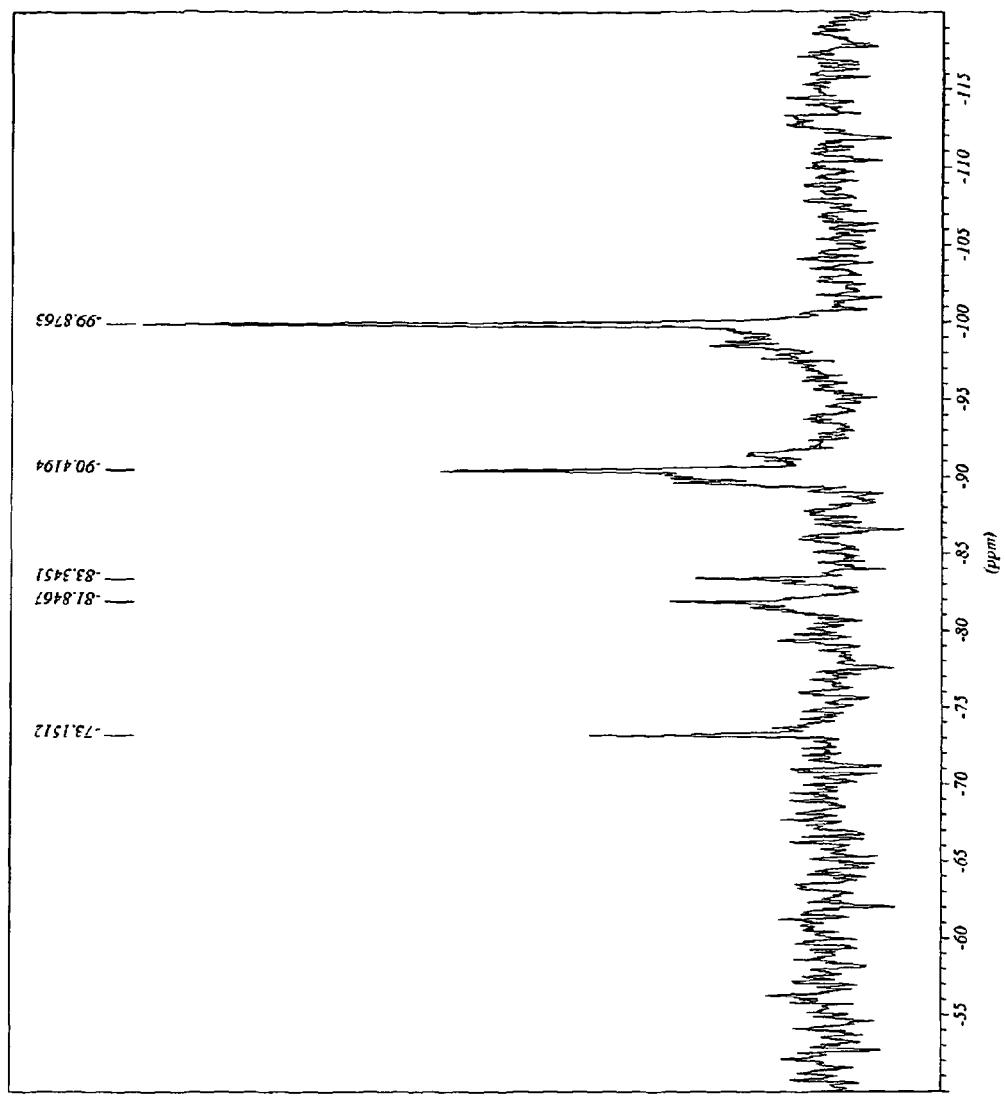

Comparison of the choline (2) silicate with silicates of (3) and (4) illustrates that as the alkyl chain length of the cations increases, so does the diversity of silicate species found within the solution (FIG. 3). Although the steric and structural differences between these cations are subtle, their effect on silicate speciation is pronounced. The ethyl derivatised choline cation (3) still shows a tendency towards the $Q^3_8$ anion. However, the presence of a substantial amount of $Q^2$ species along with clear quantities of $Q^0$, $Q^1$ and $Q^2_3$ highlights the increased diversity of silicate species expected from a TAA cation with a longer alkyl chain (FIG. 3). This effect was found to be more dramatic in the case of the propyl derivatised choline cation (4). Despite being only subtly different from cations (2) and (3), all degrees of structure control were found to have been lost when the TAA silicate was studied using NMR. No specific structural units could be identified from the spectral data obtained, which resembled that of a comparable sodium silicate solution. A broad distribution of species was found to be present suggesting that all the SDE of this particular TAA had been lost. Although such effects were likely from previously described studies, the severity and rapid loss of structure control was still unexpected to such a degree when considering the small differences between the cations tested.

With subtle changes to the cation structure, functionality and size causing such pronounced effects on anionic distribution, the expected speciation found in TAA silicates, 1:1, of (8) and (9) could be postulated. In the case of the aromatic choline derivative (8) all structure directing effects would most likely be lost and an alkali metal type distribution observed. This was found to be only partly true however, as the speciation of silicates did not mirror that of an analogous sodium silicate solution. The distribution of $Q^2$ and $Q^3$ species was 'typical' of an alkali metal silicate solution. $Q^2$ species were found to be more abundant in solution when compared to $Q^3$ but no specific structures of either type could be identified from the observed spectra, which showed only broad peaks in the relative regions of the spectral window. Interestingly, the distinct lack of smaller Q species, $Q^0$ to $Q^2_3$, was an unexpected and previously unreported effect of using such an aromatic derivatised TAA in a silicate solution. Such a link between aromatic TAA silicates and their deficiency in smaller Q species was supported by the study of a dihydroxy-aromatic functionalised TAA silicate (9). The absence of smaller anionic structures was again found suggesting that aromatic TAA cations possess a degree of structure control on silicate speciation. In addition to this, the specific structures accounting for the $Q^2$ and $Q^3$ signals could be assigned from the spectral information obtained. As highlighted in Table 1, the predominant structure found in the silicate of (9) is the $Q^3_8$ octameric species. Additionally the $Q^3_6$ hexamer and $Q^2_4$ tetramer were present and accounted for 23% and 8% of the species found in solution respectively.

As both these TAA silicates were previously unreported their effect upon silicate speciation in solution was previously unknown. As described above however, it seemed reasonable to suggest that they would display little or no control on the structural units found in their silicate solutions as they are both larger and more complex than the ethyl and propyl choline derivatives discussed above. In the case of the TAA silicate (8), the lack of smaller Q species was novel and hinted at the idea of some structure control taking place, namely a preference for larger silicate species to form in the presence of this cation. This observation was further supported by the speciation found in the TAA silicate (9), where a similar lack of smaller species was seen. This solution also showed a predominance of the $Q^3_8$ octamer which, despite the size of the alkyl groups present, suggested that structure control was indeed taking place. The SDE however, were not towards a monodispersed silicate solution, but more towards the formation of larger silicate species in solution.

Hydroxy-Functionalised TAA Silicates, (5), (6) and (7)

Having discussed the effects of increasing chain length and aromatising the TAA cation, the effects of the polyhydroxy TAA cations upon silicate speciation were not predictable. Comparison of the propyl derivatised cation (4) with the dihydroxy functionalised cation (5) would seem acceptable as the relative chain lengths in both quaternary ammonium compounds are similar. This led to a prediction that the dihydroxy cation (5) would show little or no SDE and that the silicate species present in this solution would be varied and diverse, ranging from $Q^0$-$Q^3$. This was not the case however, and the speciation found in these two solutions was very different. Rather than showing a broad distribution of many Q species, as found in the propyl derivative (4), the dihydroxy cation (5), showed the majority of silicate units to be of the $Q^3$ type, with the $Q^3_8$ octamer accounted for the entire $Q^3$ signal suggesting that rather than having no SDE, the cation (5) favoured the formation of the octameric species as previously obtained with TMA and choline.

Analysis of additional hydroxy functionalised TAA silicates, (6) and (7), showed more unexpected speciation to be present in their solutions. Despite the increased alkyl chain length, both TAA silicates contained predominantly the $Q^3_8$ structure, with the octamer accounting for at least 90% of all silicates species present in solution. These observations are against the trends discussed in the preceding paragraphs which lead to a simple suggestion. It appears that increasing alkyl chain length counteracts the SDE of TAA cations in silicate solutions. But, should these longer alkyl chains be hydroxy functionalised, then the degree of structure control increases, favouring once again the $Q^3_8$ species. The degree of structure control is not as great as in the case of TMA or choline silicates but, although measurable, the amount of $Q^0$, $Q^1$ and/or $Q^2$ present in solution is small enough to justify the idea that the cations (5), (6) and (7) exhibit SDE towards the $Q^3_8$ species in solution.

The suggestion of hydroxy-functionalisation favouring the $Q^3_8$ silicate species is further supported by the SDE observed for the dication (10). The formation of a stable TAA silicate solution containing a large and dicationic species lends itself to the potential of hydrogen bonding within silicate solutions being very important in the structure control seen and described above. It may be expected that such a sterically bulky cation would show little or no structure control but the inclusion of the hydroxy groups seems to favour once again the octameric species, which accounts for the large majority of anionic structures present.

Preparation of [Taa] [Silicate] Solutions

A series of silicate solutions were prepared using the above-mentioned TAA hydroxides. The general synthesis is described in detail for the 1:1 TMA silicate. Quantities used for the series are shown in Table 2. [(CH$_3$)$_4$N]OH 25% w/w (15 ml, 41.5 mmol) was placed in a narrow high-sided beaker and stirred using a homogeniser rotating at 11500 rpm. To this, fumed silica (2.5 g, 41.5 mmol) was added gradually over 30 minutes. The mixture was left to mix for a further 45 minutes. After a minimum of 4 days the solution was analysed by $^{29}$Si NMR. Viscosity and $^{29}$Si NMR spectroscopy data is shown in Table 3.

TABLE 2

Quantities used in the synthesis of [TAA][silicate] solutions

| Cation | Cation:Silicon | Volume [TAA][OH] | Conc. [TAA][OH] in H$_2$O | SiO$_2$ |
|---|---|---|---|---|
| 1 | 1:1 | 8.97 ml | 25% w/w | 1.5 g/25 mmol |
| 2 | 1:1 | 5.65 ml | 50% w/w | 1.5 g/25 mmol |
| 3 | 1:1 | 22 ml | 1.12M | 1.48 g/24 mmol |
| 4 | 1:1 | 24 ml | 0.91M | 1.32 g/22 mmol |
| 8 | 1:1 | 14 ml | 0.7M | 0.59 g/9.8 mmol |
| 5 | 1:1 | 11 ml | 1.6M | 1.06 g/17.6 mmol |
| 9 | 1:1 | 10 ml | 2.7M | 1.62 g/27 mmol |
| 6 | 1:1 | 6.8 ml | 3.97M | 1.62 g/27 mmol |
| 7 | 1:1 | 30 ml | 2.025M | 3.65 g/60 mmol |
| 10 | 1:1 | 27 ml | 1.51M | 4.92 g/82 mmol |

TABLE 3

Viscosity and $^{29}$Si NMR data of the silicate solutions prepared using [TAA][OH]

| Cation | Cation:Silicon | Viscosity/CPs | NMR δ($^{29}$Si)/ppm |
|---|---|---|---|
| 1 | 1:1 | 5.9 | −100.3; $Q^3_8$ Si |
| 2 | 1:1 | 6.2 | −100.3; $Q^3_8$ Si |
| 3 | 1:1 | 1.6 | −73.1; $Q^0$ Si |
|  |  |  | −81.7; $Q^1$ Si |
|  |  |  | −83.3; $Q^2_3$ Si |
|  |  |  | −90.3; $Q^2$ Si |
|  |  |  | −99.9; $Q^3_8$ Si |
| 4 | 1:1 | 1.6 | −73.1; $Q^0$ Si |
|  |  |  | −81.8; $Q^1$ Si |
|  |  |  | −83.5; $Q^2_3$ Si |
|  |  |  | −89.8; $Q^2$ Si |
|  |  |  | −99.6; $Q^3$ Si |
| 8 | 1:1 | 1.5 | −89.4; $Q^2$ Si |
|  |  |  | −99.3; $Q^3$ Si |
| 5 | 1:1 | 2.9 | −73.1; $Q^0$ Si |
|  |  |  | −90.4; $Q^2_4$ Si |
|  |  |  | −91.4; $Q^3_6$ Si |
|  |  |  | −99.8; $Q^3_8$ Si |
| 9 | 1:1 | 72.4 | −90.4; $Q^2_4$ Si |
|  |  |  | −91.2; $Q^3_6$ Si |
|  |  |  | −99.6; $Q^3_8$ Si |
| 6 | 1:1 | 65.6 | −90.0; $Q^2$ Si |
|  |  |  | −99.8; $Q^3_8$ Si |
| 7 | 1:1 | 125.9 | −73.1; $Q^0$ Si |
|  |  |  | −90.9; $Q^3_6$ Si |
|  |  |  | −99.9; $Q^3_8$ Si |
| 10 | 1:1 | 40.8 | −73.1; $Q^0$ Si |
|  |  |  | −90.7; $Q^2$ Si |
|  |  |  | −100.0; $Q^3_8$ Si |

Table 3 shows the different TAA cations and their effects on silicate speciation. It proves how the diversity and/or distribution can be tailored by selecting particular R groups present on the N$^+$ centre.

TAA Cation-Water and TAA Cation-Silicate Interactions

Although the observable effects of TAA cations within silicate solutions have been discussed above, in order to understand the nature of such chemistry, attention must be applied to the various interactions within solution. The stability of silicate species formed may be explained by considering two principal factors. Primarily, strong hydrogen-bonding between the water molecules and the silicate species are responsible for stabilising the silicate hydrates formed. Although secondary in nature, the forces between the cationic organic molecules and the water molecules and anionic silicate species are also important. Hydrogen-bonding interactions along with electrostatic interactions and van der Waals contacts influence how the organic molecules organise themselves in the solvent. This organisation is the most likely cause for the relative stability of structures observed.

For example, the TMA silicate [NMe$_4$]$_8$[Si$_8$O$_{20}$].69 H$_2$O contains a small organic cation with relatively high charge density. The cation may arrange itself within the solvent molecules of the solvated anions, hereafter referred to as the solvent shell, more easily than a larger organic cation, i.e. there is no preferred orientation of the cation in the solvent. The coulombic force generated between the cation and the silicate cube plays an important role in the stabilisation of silicate hydrates. It follows on from this suggestion, that a cation with larger organic, hydrophobic substituents will arrange themselves so as to minimise their unfavourable interaction with the polar water molecules. This change in orientation will not only affect the electrostatic interaction between silicate cage and organic cation but also the nature of the hydrogen-bonding present, as the solvent shell must adapt to the adopted geometry of the cation. This process may destabilise the silicate hydrate and hence lead to the observed loss of structure control.

Considering the above hypothesis, the increased structure control obtained by hydroxy functionalisation of larger alkyl groups may be better reasoned. The interaction between the polar water molecules and hydroxy functionalised alkyl chains will clearly have a stabilising affect to the dynamics of the hydrogen-bonded clathrate system described above. Thus, the structure control regained by hydroxy functionalisation of larger alkyl groups, it may be argued, is caused by the favourable cation-water interactions present which provide a stabilising effect on the silicate species found in solution.

Silicates Containing Mixed Cations

The distribution of soluble silicate anions in TMA silicate solutions varies with addition of sodium ions. In this study it was also suggested that should the sodium/TMA ratio exceed 2:1 then no $Q^3_8$ would be present in solution. The effect of 'sodium poisoning' on some of the new TAA cation silicates discussed earlier was not previously investigated. The focus of this investigation centres around three particular cations, TMA(1), choline(2) and (2,3-dihydroxy-propyl)-(2-hydroxy-ethyl)-dimethyl-ammonium (DPHEDMA)(7). The commercial silicate used contained a sodium/silicon ratio of 1.425:1 and displayed wide range silicate speciation as is characteristic of alkali metal silicates (Table 2). TAA cations were added so as to effect a change in cation/silicon ratio resulting in a 1:1 solution. The change in the silicate speciation was observed by NMR. The addition of sodium ions to this solution should show an increased $Q^0$ signal since the addition of alkali metal cations favours depolymerisation of the larger silicate species towards the smaller Q units. Upon initial inspection a similar effect is shown by the addition of TAA cations. In the case of TMA and choline, the $Q^2$ and $Q^3$ signals clearly account for considerably less of the observed speciation present in solution. Whereas, in all three cases, the observable $Q^4$ signal present in the starting solution has clearly been removed supporting the idea that there are no larger $Q^4$ species present in the 1:1 solutions.

More interesting is the appearance of greater fine structure upon the addition of hydroxy-functionalised TAA cations to the sodium silicate solution. This is best illustrated by the appearance of a sharp peak at −100 ppm, associated with the $Q^3_8$ octamer. Although the octamer is present in all three solutions, the speciation of silicate anions observed was largely unexpected at this (sodium/TAA/silicate) ratio. The solutions contain a cation/silicon ratio of 1:1, which is obtained by adding a quantity of TAA hydroxide in aqueous solution to a commercially available sodium silicate which contained a sodium/silicon ratio of 1:1.425. The resulting solution, in all three cases, contained a sodium/TAA ratio of 2.09:1. The effects of sodium poisoning have previously been described as being destructive to the $Q^3_8$ species and with a sodium/TAA ratio exceeding 2:1, no $Q^3_8$ would be expected. A sharp resonance associated with the octamer was observed however, and although present with varying degrees of intensity, the cubic structure was found to be present in all three solutions.

The most pronounced effect on silicate speciation was observed upon addition of the trihydroxy-cation DPHEDMA (7). Unlike the previous two examples, there was found to be little increase in the number of smaller $Q^n$ species present in solution when compared to the speciation of the starting sodium silicate. Additionally, $Q^2$ species accounted for a smaller number of anionic structures whereas no $Q^4$ structures were observed at all.

Of the $Q^3$ signal observed, over half of these species were the $Q^3_8$ octamer which contributed to 24% of all silicate species observed. This suggests that the depolymerisation of larger silicate species does occur, but rather than an increase in the number of smaller, $Q^0$, $Q^1$ and $Q^2$ species, the $Q^4$ structures which were present have formed additional $Q^3$ units, a large amount of which are the $Q^3_8$ anion. The formation of the $Q^3_8$ species in all three cases supports the role of TAA cations as structure directing agents when they are added to a sodium silicate. A newly observed effect of such TAA cations is their ability to influence the speciation of silicates even when the sodium/TAA ratio exceeds 2:1.

TABLE 2

Distribution of silicate species present in the starting sodium silicate and the three sodium/TAA mixed silicates

| Cation | Cation:Si | ≈$_c$[SiO$_2$] | pH | $Q^0$ (%) −73 ppm | $Q^1$ (%) −81/82 ppm | $Q^2_3$ (%) −83 ppm | $Q^2$ (%) −87/91 ppm | $Q^3$ (%) −100 ppm | | Additional |
|---|---|---|---|---|---|---|---|---|---|---|
| Na | 1:1.425 | 7.88M | 12 | Trace | 10.2 | 1 | 42.5 | 46.5 | $Q^4$ | Present |
| Na & (1) | 1:1 | 2.7M | 11 | 8 | 16 | 10 | 43 | 23 |  | Accounts for 8% of the total spectra observed |
| | | | | | | | | | $Q^4$ | Absent |
| Na & (2) | 1:1 | 2.0M | 10 | 12 | 21 | 9 | 43 | 15 |  | Accounts for 2.5% of the total spectra observed |
| | | | | | | | | | $Q^4$ | Absent |
| Na & (7) | 1:1 | 3.0M | 11 | 3 | 9.5 | 3 | 37 | 47.5 |  | Accounts for 24% of the total spectra observed |
| | | | | | | | | | $Q^4$ | Absent |

A similar explanation to that offered for the SDE of hydroxy functionalised TAA cations may be applied to explain these observations. As discussed previously, water plays an important role in the stability of silicate hydrates. In the case of mixed sodium/TMA silicates however, it has been reported that water may be consumed via hydration of sodium ions. The interaction of water with the sodium ions, it has been argued, disrupts the interaction between the TAA cation, the silicate anion and the solvent shell. This may be observed by the formation of lower molecular weight species within solution at the expense of the $Q^3_8$ octamer. Because of this it was reasoned that all structure control would be lost when sodium is present in more than twice the quantity of TAA. This has been shown not to be the case however, with all three mixed sodium/TAA silicate solutions showing a quantity of the $Q^3_8$ octamer to be present. A possible explanation for these observations may be found by considering the role of the hydroxy functionalised alkyl groups on the TAA cations. As the hydrogen bonding between the solvent shell and silicate anion is affected by sodium ion concentration, it seems reasonable to suggest that the hydroxy groups present on the functionalised TAA cations may adopt a similar stabilising role to that of the consumed water molecules described previously. The effects of this alternative hydrogen bonding between the hydroxy functionalised TAA cation and the depleted solvent shell may serve to stabilise the $Q^3{}_8$ octameric anion as well as the larger Q species initially present. Hence, the hydroxy functionalised TAA cations may now possess a two fold stabilising effect. The coulombic interactions ($N^+ \cdots O^-$) serve to stabilise the anionic silicate structures, particularly the $Q^3{}_8$ octamer. The hydrogen bonding however, may interact and stabilise the solvent shell, counter acting the effects of sodium poisoning. It would therefore follow, that a multi functionalised TAA cation would show the greatest degree of structure control and stabilisation upon a mixed sodium/TAA silicate.

This was found to be the case as the TAA cation, DPHEDMA (7), showed the greatest quantity of the $Q^3{}_8$ octamer to be present when added to a commercial sodium silicate. As described above, the speciation present in this mixed solution showed quite different character when compared to the mixed sodium/TMA and sodium/choline silicates. Following from this, it may be expected that the quantity and intensity of the $Q^3{}_8$ octamer would decrease as the TAA functionalisation was reduced, being lowest for the mixed sodium/TMA silicate solution. This was not found to be the case however, with the sodium/choline silicate showing the least $Q^3{}_8$ character. This inconsistent result may be due to the low silica concentration present in the sodium/choline solution. It has been shown, that in a sodium silicate solution of decreasing silica concentration, the speciation of anionic structures favours smaller $Q^n$ species to be present. The concentration of silica in the mixed sodium/choline is relatively low, and may explain the distribution of silicate species observed. A sodium silicate of comparable silica concentration may similarly be expected to show predominantly smaller $Q^n$ species. The structure control provided by the addition of the choline cation has shown itself to be present in the form of a small percentage of $Q^3{}_8$ formed. The effect may be less pronounced however, due to the dilute nature of the silicate solution and the sodium content therein.

The newly observed effects of structure control on sodium silicate solution upon addition of TMA hydroxide may also be in some part due to the water content of the final solution. The TMA hydroxide was added as a 25% w/w solution to the commercial sodium silicate. The mixture formed was not stable and readily formed a precipitate which was found to re-dissolve upon addition of water. The addition of water to the solution may provide sufficient water molecules to both hydrate the sodium ions while maintaining the solvent shell around the TMA cation. Thus the silicate structure remains stabilised but also speciation is shifted towards the $Q^3{}_8$ anion due to the SDE of the TAA cation.

A similar observation was made when studying a synthetic silicate containing mixed cationic content. A solution of sodium hydroxide was mixed with a solution of TMA hydroxide so that the molar ratio of sodium/TMA was 1:1. The mixed solution was then used to synthesise a mixed silicate containing a cation/silica ratio of 1:1. The resulting solution showed a broad distribution of silicate species to be present with those of a $Q^2$ nature being most abundant. Due to the quantities of TMA present however, a substantial quantity of the $Q^3{}_8$ anion was observed which, even in a solution containing equal quantities of sodium, was not expected due to the poisoning effects described in the literature. It seems reasonable to therefore suggest that, although sodium poisoning will affect silicate speciation, the silica concentration and nature of the TAA cation may counteract the loss of structure control observed in earlier studies.

The Effect of Temperature on Silicate Speciation

Figure 4:
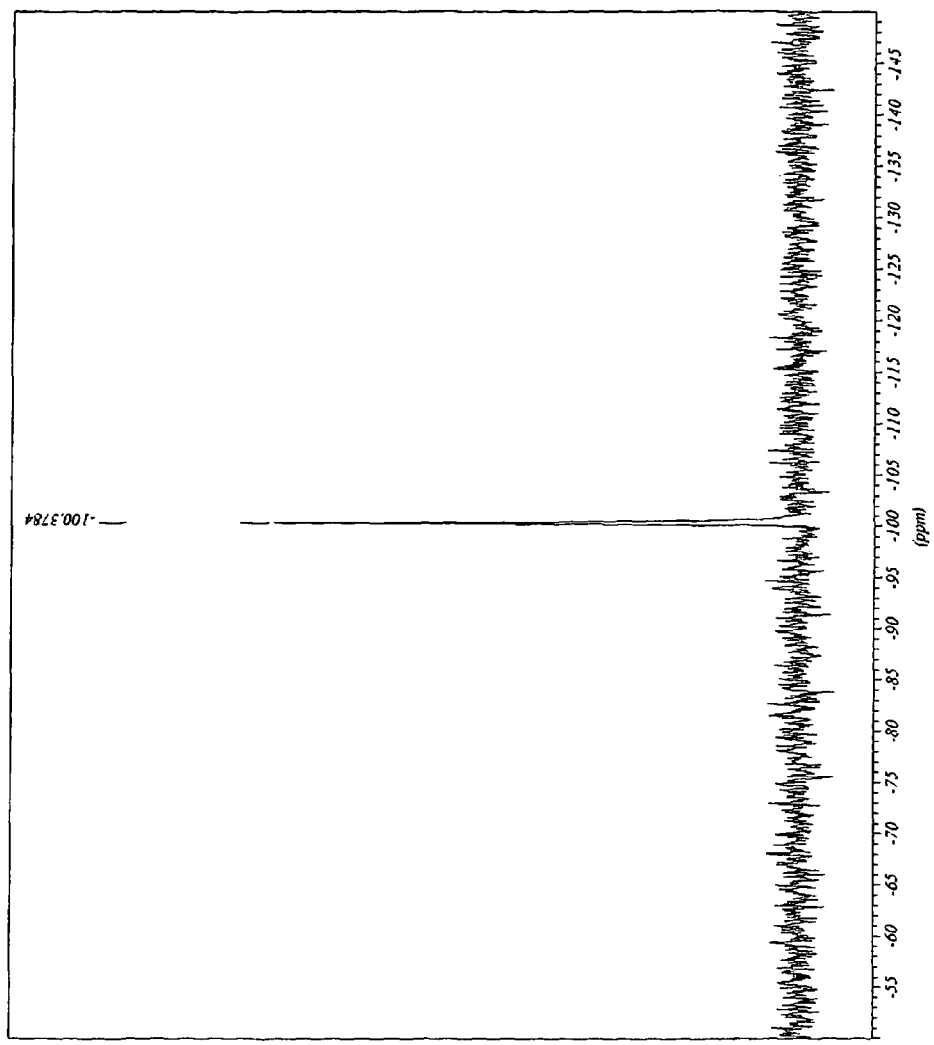
FIG. 4 shows $^{29}$Si NMR spectra of (a) TMA silicate solution 1:1 and (b) the same solution after having been heated for 1 hour at 75° C.
Figure 4:
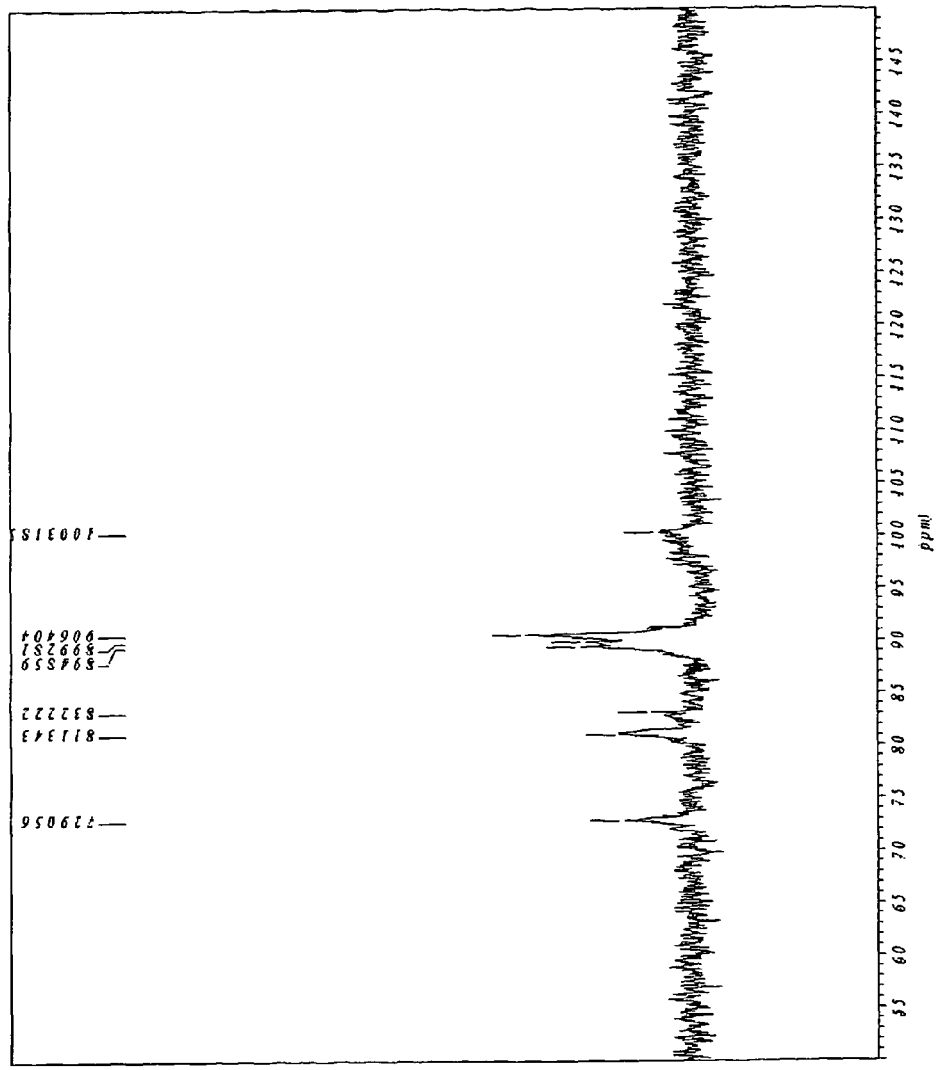

The relationship between sodium/TAA content within mixed silicates has already shown some interesting, newly observed effects. Solutions of TMA, Choline and DPHEDMA silicate were synthesised with a cation/silicon ratio of 1:1. The effect of temperature upon silicate speciation, within these solutions, was investigated by $^{29}$Si NMR. The change of silicate speciation within a TMA silicate is quite pronounced (FIG. 4). In this 1:1 solution, as described previously, the single silicate structure found is that of the $Q^3{}_8$ octamer (FIG. 4a). This solution was then heated on a water bath at 75° C. for 1 hour. The silicate speciation was found to have significantly changed within this time period (FIG. 4b). The distribution of silicates found within the post heated solution showed a large degree of thermal rearrangement had taken place. Unlike the monodispersed starting solution, the resultant speciation shows a profile more closely associated with that of an alkali metal silicate. The $^{29}$Si NMR shows a percentage of $Q^0$, $Q^1$, $Q^2$ and $Q^3$ to be present. The most intense peak observed appears at $\delta=-90.6$ ppm and is rather broad. This suggests that the majority of silicate structures have rearranged to a $Q^2$ type geometry and not a $Q^3{}_6$ type structure although the presence of the prismatic hexamer may not be ruled out. In addition to this, there are a significant number of $Q^0$ and $Q^1$ structures present along with a small quantity of $Q^3$. The residual $Q^3$ peak is also broad suggesting that the $Q^3$ structures which are present are not solely the $Q^3{}_8$ octamer.

Interestingly, there is no observable $Q^4$ signal in either of the spectra. Although a large degree of silicate redistribution has occurred there are no $Q^4$ type species observed before or after the heating of the solution. This observation supports the idea that thermal instability will favour the formation of smaller silicate species as the structure control is lost within a TMA silicate solution. Should a random redistribution of silicate structures occur it might be expected that some smaller silicate structures may agglomerate giving rise to a $Q^4$ type signal. This has not been observed however, with the $^{29}$Si NMR spectrum showing an increased intensity for smaller silicate species only. These smaller species have been formed at the apparent expense of the $Q^3{}_8$ octamer. Accordingly, there is a redistribution of silicate species, along with an associated loss of structure control.

Figure 5:
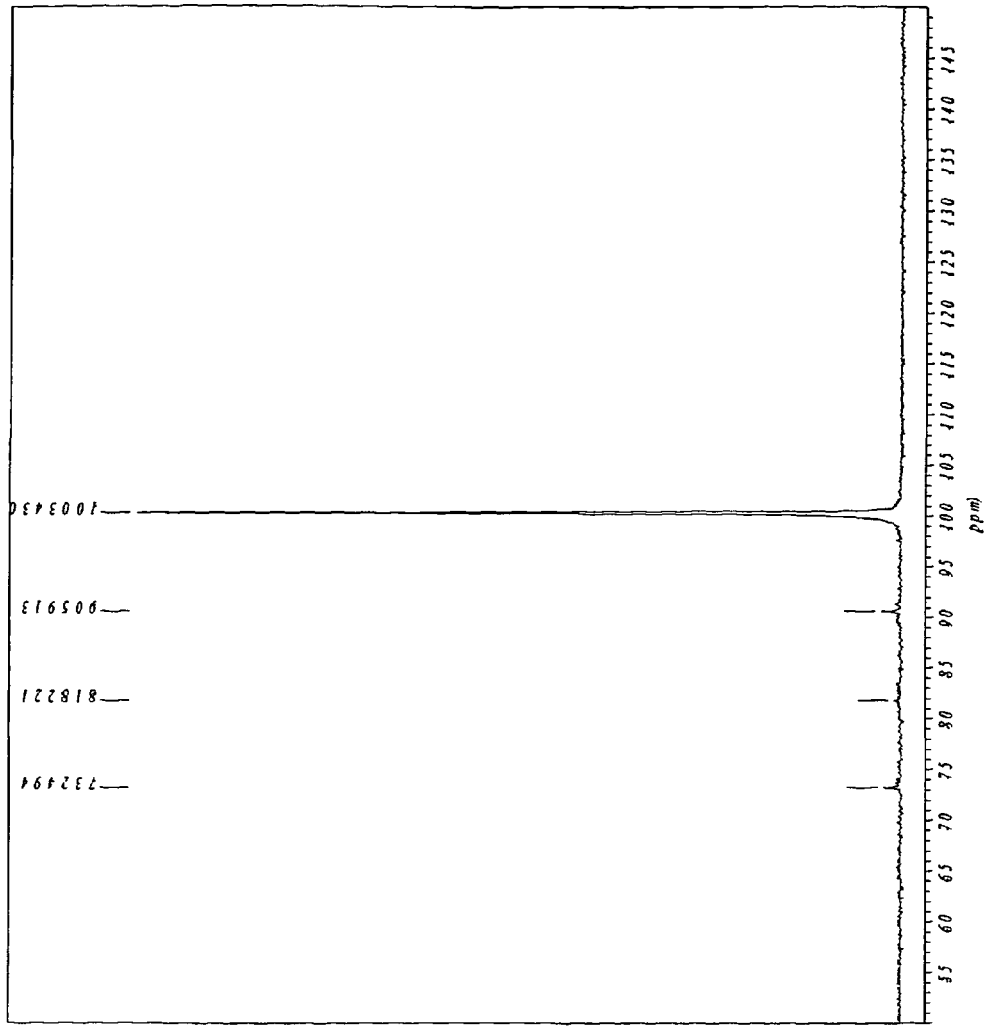
FIG. 5 shows $^{29}$Si NMR spectra of (a) Choline silicate solution 1:1 and (b) the same solution after having been heated for 1 hour at 75° C.
Figure 5:
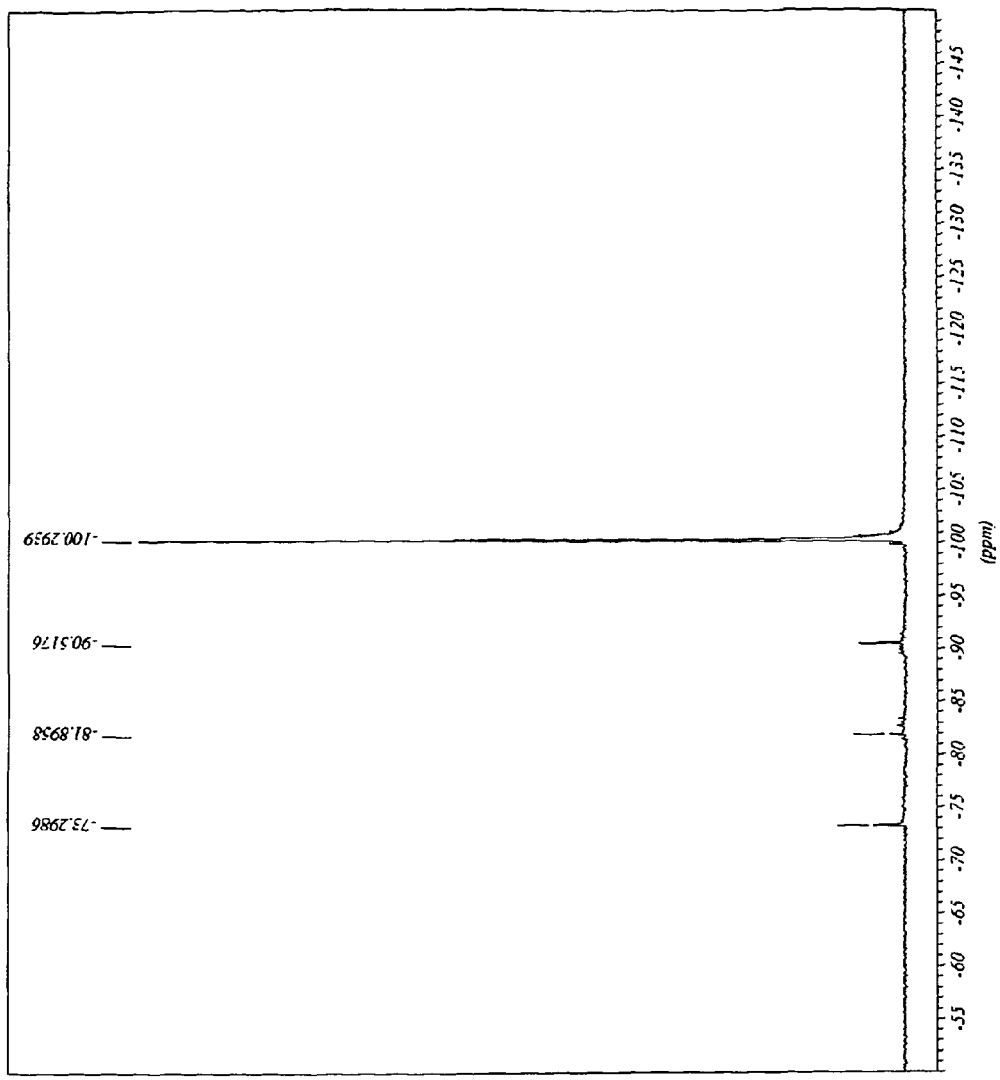
Figure 6:
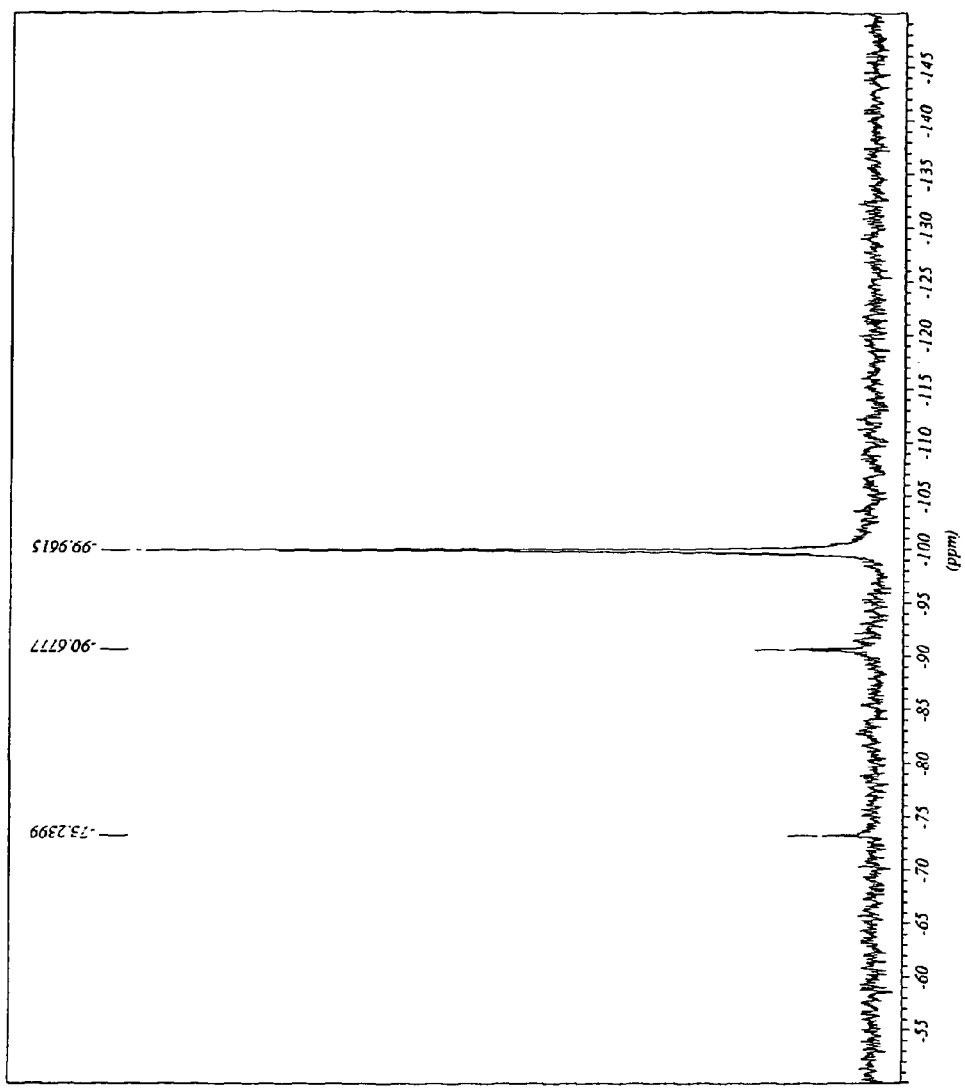
FIG. 6 shows $^{29}$Si NMR spectra of (a) DPHEDMA silicate solution 1:1 and (b) the same solution after having been heated for 1 hour at 75° C.
Figure 6:
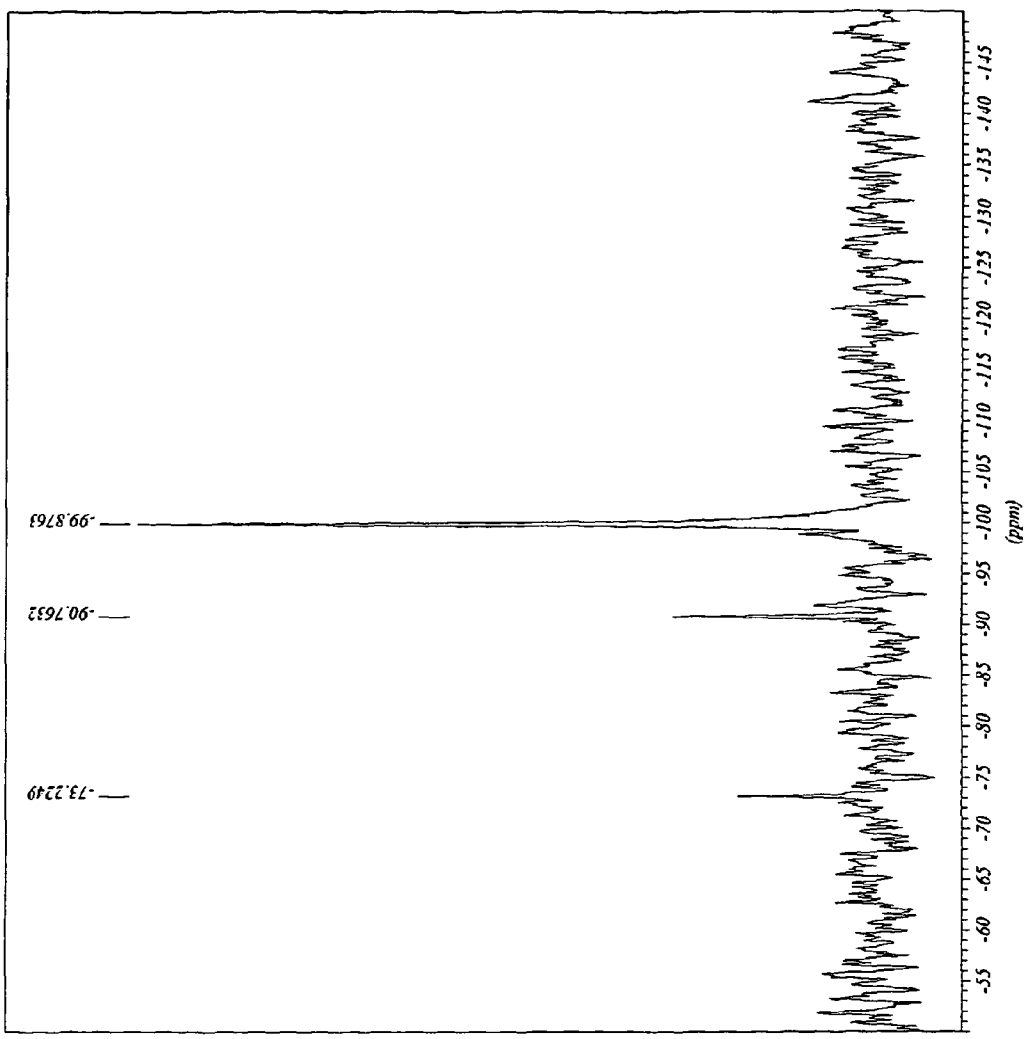

The behaviour of analogous choline and DPHEDMA silicate solutions under identical conditions could not be more different. As with the example of TMA silicate described above, the thermal stability of these two silicate solutions was investigated by $^{29}$Si NMR. Spectra were recorded of the starting solutions and then again after they had been heated to a temperature of 75° C. for one hour (FIG. 5 & FIG. 6). The speciation found within all three solutions before and after heat treatment is tabulated in Table 3.

The procedures for preparing these three silicate solutions are shown below:

TMA: [(CH$_3$)$_4$N]OH 25% w/w (15 ml, 41.5 mmol) was placed in a narrow high-sided beaker and stirred using a homogeniser rotating at 11500 rpm. To this, fumed silica (2.5 g, 41.5 mmol) was added gradually over 30 minutes. The mixture was left to mix for a further 45 minutes. After a minimum of 4 days the solution was analysed by $^{29}$Si NMR.

Choline: [(CH$_3$)$_3$N(CH$_2$CH$_2$OH)][OH] 50% w/w (5.65 ml, 25 mmol) was placed in a narrow high-sided beaker and stirred using a homogeniser rotating at 11500 rpm. To this, fumed silica (1.5 g, 25 mmol) was added gradually over 30 minutes. The mixture was left to mix for a further 45 minutes. After a minimum of 4 days the solution was analysed by $^{29}$Si NMR.

DPHEDMA: [(CH$_3$)$_2$N(CH$_2$CH$_2$OH)(CH$_2$CHOHCH$_2$OH)]OH 2.025M (30 ml, 60 mmol) was placed in a narrow high-sided beaker and stirred using a homogeniser rotating at 11500 rpm. To this, fumed silica (3.65 g, 60 mmol) was added gradually over 30 minutes. The mixture was left to mix for a further 45 minutes. After a minimum of 4 days the solution was analysed by $^{29}$Si NMR.

tion was added choline hydroxide, [(CH$_3$)$_3$N(CH$_2$CH$_2$OH)][OH], 8.2 mmol. An analogous solution containing sodium hydroxide, 8.2 mmol, was prepared at the same time. These two solutions along with the base material described were dried to produce a fire resistant glass laminate. These laminates were stored at an elevated temperature of at least 75° C. The haze of the glass laminated structures was measured at

TABLE 3

Speciation of silicate species within TAA silicates before and after heating for 1 hour at 75° C.

| Cation | Cation:Si | ≈$_c$[SiO$_2$] | $Q^0$ (%) −73 ppm | $Q^1$ (%) −81/82 ppm | $Q^2_3$ (%) −83 ppm | $Q^2$ (%) −87/91 ppm | $Q^3$ (%) −100 ppm | | Additional |
|---|---|---|---|---|---|---|---|---|---|
| TMA | 1:1 | 2.78M | 0 | 0 | 0 | 0 | 100 | $Q^3_8$ | Accounts for all the $Q^3$ Signal observed |
|  |  |  |  |  |  |  |  | $Q^4$ | Absent |
| TMA After Heating | 1:1 | 2.78M | 5.4 | 9.6 | 2.7 | 79 | 4.1 |  | Slightly broad signals observed |
|  |  |  |  |  |  |  |  | $Q^4$ | Absent |
| Choline | 1:1 | 2.42M | Trace | Trace | Trace | Trace | 100 | $Q^3_8$ | Accounts for all the $Q^3$ Signal observed |
|  |  |  |  |  |  |  |  | $Q^4$ | Absent |
| Choline After Heating | 1:1 | 2.42M | Trace | Trace | Trace | Trace | 100 |  | No Observable change in speciation |
| DPHEDMA | 1:1 | 2.42M | 4 | 0 | 0 | 5 | 91 | $Q^3_6$ | Accounts for 5% |
|  |  |  |  |  |  |  |  | $Q^3_8$ | Accounts for all the $Q^3$ Signal observed |
|  |  |  |  |  |  |  |  | $Q^4$ | Absent |
| DPHEDMA After Heating | 1:1 | 2.42M | 4 | 0 | 0 | 5 | 91 |  | No Observable change in speciation |

As shown, the larger, hydroxy functionalised, TAA silicates have undergone no thermal rearrangement. The speciation observed within both solutions before and after heating overwhelmingly favours the $Q^3_8$ octameric anion. This observation suggests that, in the case of these two hydroxy functionalised TAA silicates at least, the solutions are thermally stable to a temperature of 75° C. This behaviour is clearly different from that of TMA silicate solution and again, this increased stability may be attributed to the interaction of additional hydrogen bonding. The stability of silicate species with respect to the TAA/silicate/water system has been described above, but the increased thermal stability of the two functionalised TAA silicates may be explained in a similar manner. The hydrogen bonding between the solvent shell and the hydroxy functionalised TAA cations may be serving to stabilise the $Q^3_8$ structure more so than in the previously studied TMA silicate. This additional interaction has been found to increase the thermal stability of choline and DPHEDMA silicates.

The heat treated TMA silicate (FIG. 4) did not show any further silicate redistribution after cooling even after a period of four weeks. This observation suggests that the thermal instability described above results in a permanent redistribution of silicate anions within solution. The speciation of silicate anions observed within a heated sample of TMA silicate 1:1, seems to be as a result of a number of decomposition reactions rather than thermal rearrangement. The type of decomposition reaction taking place may not be categorically inferred from the spectroscopic evidence. However, the redistribution of anions observed is clearly not a reversible process and hence, the processes involved within the thermal rearrangement observed are not a matter of solely kinetics as should this be the case, the thermodynamic product, $Q^3_8$, would be expected to reform after time.

The Thermal Stability of Glazings According to the Invention

A sodium silicate solution, molar ratio 3.41:1, containing 7.24% glycerol solution, was prepared. To 297 g of this soluthe start of the test and after a period of 30 days using a Hazeguard Dual hazemeter. The results are shown below in Table 4:—

TABLE 4

Thermal stability of a glazing according to the invention in comparison with a control glazing (base solution) and a glazing with sodium hydroxide added

| Laminate interlayer composition | Haze as measured at the start of the test | Haze as measured after a period of 30 days at elevated temperature |
|---|---|---|
| Base solution | 0.16% | 41.3% |
| Solution + Sodium Hydroxide | 0.26% | 48.3% |
| Solution + Choline Hydroxide | 0.36% | 36.5% |

Table 4 shows the increased thermal stability of the glazing with an interlayer comprising choline hydroxide in comparison with glazings with interlayers where nothing is added (base solution) and where sodium hydroxide is added. The base silicate is in the middle of the other two results. Adding an alkali metal cation makes the ageing worse (increased haze measurement) but adding a hydroxyl functionalised TAA cation (choline) clearly improves the ageing performance.

A similar test was carried out using a different sodium silicate solution, of molar ratio 3.97:1, containing 5% glycerol solution. To 297 g of this solution was added choline hydroxide, [(CH$_3$)$_3$N(CH$_2$CH$_2$OH)][OH], 8.2 mmol. An analogous solution containing sodium hydroxide, 8.2 mmol, was prepared at the same time. These two solutions along with the base material described were dried to produce a fire resistant glass laminate. These laminates were stored at an elevated temperature of at least 75° C. The haze of the glass laminated structures was measured at the start of the test and after a period of 20 days using a Hazeguard Dual hazemeter. The results are shown below in Table 5:—

TABLE 5

Thermal stability of a glazing according to the invention in comparison with a control glazing (base solution) and a glazing with sodium hydroxide added

| Laminate interlayer composition | Haze as measured at the start of the test | Haze as measured after a period of 20 days at elevated temperature |
| --- | --- | --- |
| Base solution | 0.11% | 19.0% |
| Solution + Sodium Hydroxide | 0.13% | 19.5% |
| Solution + Choline Hydroxide | 0.30% | 5.36% |

Table 5 shows that the improved ageing performance can be obtained using a different silicate as a starting point, hence showing the adaptability of the invention and reproducibility of the results.

CONCLUSIONS

A series of TAA hydroxides were synthesised and used to prepare ten TAA silicate solutions. The distribution of silicate species within these silicate solutions was then investigated by $^{29}$Si NMR and found to be directly related to the nature and quantity of the TAA cation present.

It was found that hydroxy-functionalisation of the longer alkyl chains upon the ammonium cations has a favourable effect towards the structure directing effects of the TAA cations, particularly when compared to analogous TAA silicates. It was found that the hydroxy functionalised cation, DPHEDMA, exerted a pronounced degree of structure control when added to a sodium silicate solution. TMA, choline and DPHEDMA were found to exert some SDEs on a sodium silicate despite being present in relatively small quantities, showing them to be less susceptible to the effects of sodium poisoning than had been previously reported.

In the case of choline and DPHEDMA silicate the $Q^3_8$ octamer, found in many of the novel TAA silicates, was found to be the thermodynamic product. These two TAA silicates also showed much greater thermal stability when compared with previous studies on TMA silicate. Furthermore, the speciation within a dried silicate has been seen to be directly related to the distribution of silicate species observed within the initial aqueous silicate solution. Interlayers comprising additives according to the invention demonstrate improved thermal stability and ageing performance.

The invention claimed is:

1. A stable aqueous solution for the production of fire resistant glazings comprising:
   at least one alkali metal silicate;
   water; and
   at least one additive comprising a quaternary ammonium compound having the general formula 1:

$R_1R_2R_3R_4N^+OH^-$         1 wherein $R_1$, $R_2$, $R_3$ and $R_4$ which may be the same or different represent alkyl groups, hydroxy-substituted alkyl groups, alkaryl groups, hydroxy-substituted alkaryl groups comprising from 1 to 12 carbon atoms, or groups having the general formula —[CH$_2$]n-N$^+$R$_5$R$_6$R$_7$ wherein n is an integer having a value of from 1 to 12, the group —[CH$_2$]n- may be hydroxy-substituted, and $R_5$, $R_6$ and $R_7$ which may be the same or different represent alkyl groups, hydroxy-substituted alkyl groups, alkaryl groups or hydroxy-substituted alkaryl groups comprising from 1 to 12 carbon atoms;
   with the proviso that at least one of the groups $R_1$, $R_2$, $R_3$, $R_4$, $R_5$, $R_6$ and $R_7$ represents a hydroxy-substituted alkyl group or a hydroxy-substituted alkaryl group comprising at least 2 carbon atoms wherein the hydroxy substituent is not located on a carbon atom which is bonded to a nitrogen atom; and wherein
   the additive comprises at least two hydroxy substituents; and
   at least one of the groups $R_{1-7}$ comprises at least two hydroxy substituents.

2. The aqueous solution according to claim 1, wherein $R_1$, $R_2$, $R_3$ and $R_4$ which may be the same or different represent alkyl groups, hydroxy-substituted alkyl groups, alkaryl groups, or hydroxy-substituted alkaryl groups comprising from 1 to 8 carbon atoms.

3. The aqueous solution according to claim 1, wherein $R_1$, $R_2$, $R_3$ and $R_4$ which may be the same or different represent alkyl groups, hydroxy-substituted alkyl groups, alkaryl groups, or hydroxy-substituted alkaryl groups comprising from 3 to 8 carbon atoms.

4. The aqueous solution according to claim 1, wherein the additive is present in an amount of from 0.01 to 10% by weight of the solution.

5. A transparent intumescent interlayer for the production of fire resistant glazings comprising:
   at least one alkali metal silicate,
   water; and
   at least one additive comprising a quaternary ammonium compound having the general formula 1:

$R_1R_2R_3R_4N^+OH^-$        1 wherein $R_1$, $R_2$, $R_3$ and $R_4$ which may be the same or different represent alkyl groups, hydroxy-substituted alkyl groups, alkaryl groups, hydroxy-substituted alkaryl groups comprising from 1 to 12 carbon atoms, or groups having the general formula —[CH$_2$]n-N$^+$R$_5$R$_6$R$_7$ wherein n is an integer having a value of from 1 to 12, the group —[CH$_2$]n- may be hydroxy-substituted, and $R_5$, $R_6$ and $R_7$ which may be the same or different represent alkyl groups, hydroxy-substituted alkyl groups, alkaryl groups or hydroxy-substituted alkaryl groups comprising from 1 to 12 carbon atoms;
   with the proviso that at least one of the groups $R_1$, $R_2$, $R_3$, $R_4$, $R_5$, $R_6$ and $R_7$ represents a hydroxy-substituted alkyl group or a hydroxy-substituted alkaryl group comprising at least 2 carbon atoms wherein the hydroxy substituent is not located on a carbon atom which is bonded to a nitrogen atom; and wherein
   the additive comprises at least two hydroxy substituents; and
   at least one of the groups $R_{1-7}$ comprises at least two hydroxy substituents.

6. The interlayer according to claim 5, wherein the interlayer comprises from 10 to 50% by weight of water.

7. A fire resistant glazing comprising at least one interlayer according to claim 5 attached to at least one glass sheet.

8. A fire resistant glazing assembly comprising at least one fire resistant glazing according to claim 7 attached to a frame.

* * * * *